(12) United States Patent
Mun et al.

(10) Patent No.: US 11,339,132 B2
(45) Date of Patent: May 24, 2022

(54) COMPOUND FOR ORGANIC ELECTRIC ELEMENT, ORGANIC ELECTRIC ELEMENT COMPRISING THE SAME, AND ELECTRONIC DEVICE THEREOF

(71) Applicant: DUK SAN NEOLUX CO., LTD., Cheonan-si (KR)

(72) Inventors: Soung Yun Mun, Cheonan-si (KR); Sun-Hee Lee, Hwaseong-si (KR); Bumsung Lee, Hwaseong-si (KR); Junghwan Park, Hwaseong-si (KR); Gyu Min Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 979 days.

(21) Appl. No.: 16/071,233

(22) PCT Filed: Dec. 30, 2016

(86) PCT No.: PCT/KR2016/015544
§ 371 (c)(1),
(2) Date: Jul. 19, 2018

(87) PCT Pub. No.: WO2017/126818
PCT Pub. Date: Jul. 27, 2017

(65) Prior Publication Data
US 2021/0198214 A1 Jul. 1, 2021

(30) Foreign Application Priority Data
Jan. 21, 2016 (KR) .................. 10-2016-0007574

(51) Int. Cl.
*C07D 239/84* (2006.01)
*C07D 401/12* (2006.01)
(Continued)

(52) U.S. Cl.
CPC ......... *C07D 239/84* (2013.01); *C07D 401/12* (2013.01); *C07D 403/04* (2013.01);
(Continued)

(58) Field of Classification Search
CPC .. C07D 239/84; C07D 401/12; C07D 403/04; C07D 403/12; C07D 405/12;
(Continued)

(56) References Cited

U.S. PATENT DOCUMENTS

2017/0125699 A1\* 5/2017 Ahn ................ H01L 51/0071

FOREIGN PATENT DOCUMENTS

| CN | 102625806 A | 8/2012 |
| CN | 103249722 A | 8/2013 |

(Continued)

OTHER PUBLICATIONS https://spie.org/news/5197-transparent-organic-leds-for-new-lighting-applications?SSO=1 (Year: 2013).\*
(Continued)

*Primary Examiner* — Vu A Nguyen
(74) *Attorney, Agent, or Firm* — Vorys, Sater, Seymour & Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

10 Claims, 1 Drawing Sheet

(51) Int. Cl.

| | |
|---|---|
| *C07D 405/12* | (2006.01) |
| *C07D 405/14* | (2006.01) |
| *C07D 409/12* | (2006.01) |
| *C07D 409/14* | (2006.01) |
| *C07D 403/12* | (2006.01) |
| *C07D 403/14* | (2006.01) |
| *C07D 491/048* | (2006.01) |
| *H01L 51/00* | (2006.01) |
| *H01L 51/50* | (2006.01) |
| *C07D 403/04* | (2006.01) |

(52) U.S. Cl.
CPC ......... *C07D 403/12* (2013.01); *C07D 405/12* (2013.01); *C07D 405/14* (2013.01); *C07D 409/12* (2013.01); *C07D 409/14* (2013.01); *C07D 491/048* (2013.01); *H01L 51/0061* (2013.01); *H01L 51/0072* (2013.01); *H01L 51/0073* (2013.01); *H01L 51/0074* (2013.01); *H01L 51/5056* (2013.01)

(58) Field of Classification Search
CPC .. C07D 405/14; C07D 409/12; C07D 409/14; C07D 491/048; H01L 51/0061; H01L 51/0072; H01L 51/0073; H01L 51/0074
See application file for complete search history.

(56) References Cited

FOREIGN PATENT DOCUMENTS

| | | |
|---|---|---|
| CN | 104471026 A | 3/2015 |
| KR | 10-2011-0057078 A | 5/2011 |
| KR | 10-2015-0042387 A | 4/2015 |
| KR | 10-2015-0111106 A | 10/2015 |
| KR | 10-2015-0127548 A | 11/2015 |
| KR | 10-2015-0130928 A | 11/2015 |
| KR | 10-2015-0135123 A | 12/2015 |
| KR | 20150144121 A * | 12/2015 |
| KR | 20160143496 A * | 12/2016 |
| TW | 201226398 A | 7/2012 |
| WO | 2015/053572 A1 | 4/2015 |
| WO | 2015/170882 A1 | 11/2015 |
| WO | 2015/174738 A1 | 11/2015 |
| WO | 2015/178732 A1 | 11/2015 |

OTHER PUBLICATIONS

Computer-generated English-language translation of KR-20150144121-A.*
Computer-generated English-language translation of KR-20160143496-A.*
The Office Action dated Dec. 27, 2018 for corresponding CN 201601033608.0, 66 pages.
Chinese Office Action for corresponding Chinese Patent Application No. 201610133608.0; dated Nov. 2019; five pages.

* cited by examiner

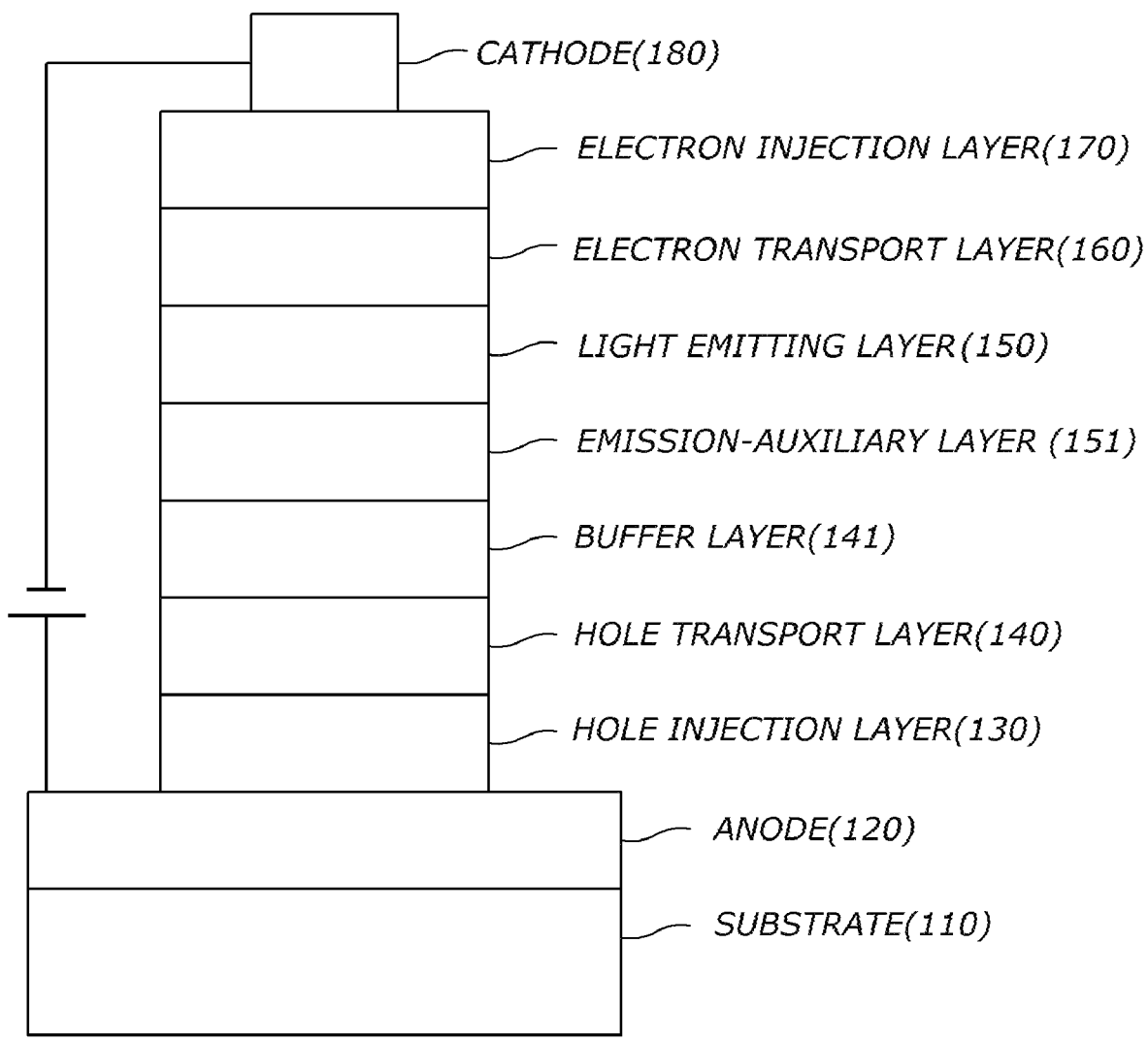

COMPOUND FOR ORGANIC ELECTRIC ELEMENT, ORGANIC ELECTRIC ELEMENT COMPRISING THE SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2016-0007574, filed on Jan. 21, 2016, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed between them. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there are problems of shift of a maximum luminescence wavelength to a longer wavelength due to intermolecular interactions, of deterioration in color purity, and lowering the efficiency of the device due to an effect of luminous reduction. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according to the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Therefore, it is necessary to develop a light emitting material having a high thermal stability and achieving a charge balance in the light emitting layer efficiently.

Further, recently, in order to solve the emission problem in a hole transport layer and driving voltage of an organic electric element, it is preferable to form an emission-auxiliary layer between the hole transport layer and a light emitting layer, and it is necessary to develop different emission-auxiliary layers according to respective light emitting layers (R, G, B).

In general, an electron which is transferred from an electron transport layer to a light emitting layer and a hole which is transferred from a hole transport layer to the light emitting layer are recombined to form an exciton.

However, most of the materials used for the hole transport layer have a low T1 value since they have a low HOMO value. As a result, the excitons generated in the light emitting layer are transferred to the hole transport layer, resulting in a charge unbalance in the light emitting layer and light is emitted in or at the interface of the hole transport layer, and thus color purity, luminous efficiency and lifetime are lowered.

In addition, when a material having high hole mobility is used in order lower a driving voltage, the efficiency tends to decrease. This is because the hole mobility is faster than the electron mobility in a general organic electroluminescent device, resulting in a charge unbalance in the light emitting layer, and thus efficiency and lifetime are lowered.

Therefore, the material of an emission-auxiliary layer should have to a hole mobility (within the full device blue device driving voltage range), high electron (electron block) values and wide band gaps so as to have a proper driving voltage for solving the problems of the hole transport layer. However, this cannot be achieved simply by the structural properties of the core of an emission-auxiliary layer material and this can be achieved when the characteristics of the core and the sub-substituent of the material are combined properly. Therefore, in order to improve efficiency and lifetime of an organic electric element, there are strong needs to develop material of the emission-auxiliary layer having high T1 value and wide band gap.

That is, in order to allow an organic electric element to fully exhibit excellent features, it should be prerequisite to support a material constituting an organic material layer in the element, for example, a hole injection material, a hole transport material, a light emitting material, an electron transport material, by a stable and efficient material. However, development of an organic material layer material for an organic electric device has not been sufficiently developed yet. Therefore, there is a continuous need to develop new materials, in particular, there are strong needs to develop host material for a light emitting layer and material of the emission-auxiliary layer.

Object, Technical Solution and Effects of the Invention

The present invention is to provide a compound lowering a driving voltage, improving luminous efficiency, color purity and lifetime of the element, an organic electric element comprising the same, and an electronic device thereof.

In an aspect of the present invention, the present invention provides the compound represented by the following formula.

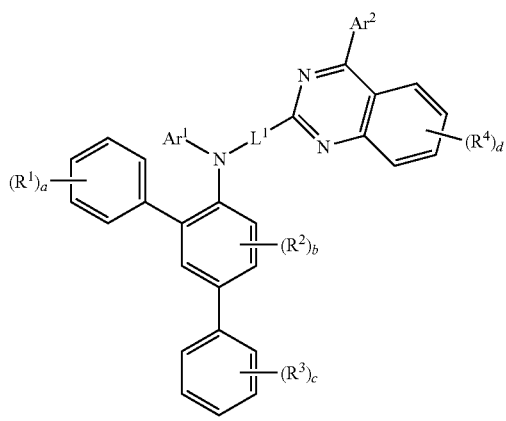

In another aspect of the present invention, the present invention provides an organic electric element using the compound represented by formula above and an electric device thereof.

By using the compound according to embodiments of the present invention, a driving voltage can be lowered and the luminous efficiency and lifetime of the element can be improved.

BRIEF DESCRIPTION OF THE DRAWING

The FIGURE illustrates an example of an organic electric light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, embodiments of the present invention will be described in detail with reference to the accompanying drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine(F), bromine(Br), chlorine(Cl) or iodine(I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), or an alkyl group substituted with a cycloalkyl or with a cycloalkyl substituted with an alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises spiro compound formed by linking R and R' together with the carbon bonded to them.

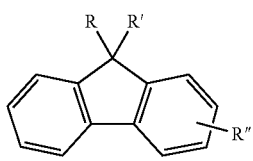

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

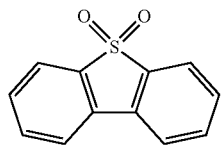 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted with deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

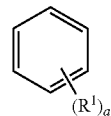

Here, the substituent $R^1$ is absent when a is an integer of zero, the sole $R^1$ is linked to any one of the carbon atoms constituting the benzene ring when a is an integer of 1. Further, when a is an integer of 2 or 3, the substituent $R^1$s are linked to the benzene ring as follows and they are the same and different, and the substituents $R^1$s may be linked to the benzene ring in a similar manner to that when a is an integer of 4 to 6. Further, hydrogen atoms linked to carbon constituents of the benzene ring may be omitted.

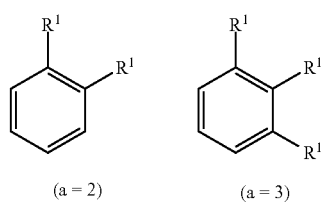

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown in FIGURE, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the inventive compound may be used as material of the light emitting layer 150, a hole transport layer 140 and/or an emission-auxiliary layer 151, preferably, as material of the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, energy level and $T_1$ value between the respective layers of the organic material layer, inherent material properties (mobility, interfacial properties, etc.) and the like can be optimized by forming a light emitting layer 150 with the compound represented by the Formula 1 of the present invention, resulting in improving simultaneously the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G(Green), B(Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by the following formula 1.

[Formula 1]

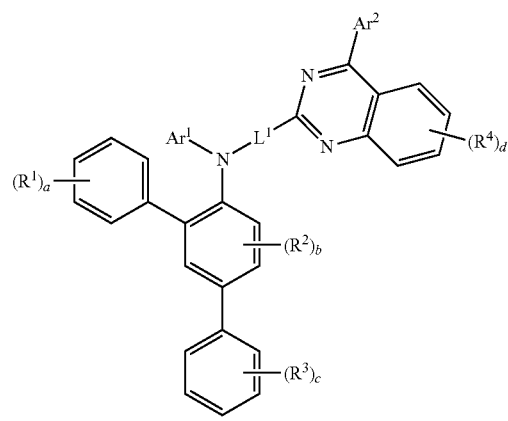

In the formula 1, each of symbols may be defined as follows.

Ar$^1$ and Ar$^2$ may be each independently selected from the group consisting of hydrogen, halogen, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group, a C$_6$-C$_{30}$ aryloxy group and -L'-N(R$_a$)(R$_b$).

When Ar$^1$ and Ar$^2$ are an aryl group, they may be preferably a C$_6$-C$_{30}$ aryl group, more preferably a C$_6$-C$_{12}$ aryl group, for example, phenyl, biphenyl, naphthyl, or the like; when Ar$^1$ and Ar$^2$ are a heterocyclic group, they may be preferably a C$_2$-C$_{30}$ heterocyclic group, more preferably a C$_2$-C$_{12}$ heterocyclic group, for example, pyridine, carbazole, dibenzothiophene, dibenzofuran, benzoquinazoline, or the like; when Ar$^1$ and Ar$^2$ are a fluorenyl group, they may be 9,9-dimethyl-9H-fluorene, 9,9-diphenyl-9H-fluorene or the like.

R$^1$ to R$^4$ may be each independently selected from the group consisting of hydrogen, deuterium, halogen, S(R$^5$), O(R$^6$), N(R$^7$)(R$^8$), C(R$^9$)(R$^{10}$)(R$^{11}$), a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group, a C$_6$-C$_{30}$ aryloxy group and -L'-N(R$_a$)(R$_b$), When R$^1$ to R$^4$ are an aryl group, they may be preferably a C$_6$-C$_{30}$ aryl group, more preferably a C$_6$-C$_{12}$ aryl group, for example, phenyl, biphenyl, naphthyl, or the like.

Further, neighboring R$^1$ groups, neighboring R$^2$ groups, neighboring R$^3$ groups, or neighboring R$^4$ groups, and Ar$^1$ and R$^1$, Ar$^1$ and R$^2$, Ar$^2$ and R$^4$, R$^1$ and R$^2$, or R$^2$ and R$^3$ are optionally linked to each other to form a ring, preferably, an aliphatic ring, an aromatic ring, a heterocyclic group or a fused ring group thereof, or the like. More preferably, the ring may be selected from the group consisting of a C$_6$-C$_{60}$ aryl(arylene) group, a fluorenyl(fluorenylene) group, a C$_2$-C$_{60}$ heterocyclic group containing at least one heteroatom selected from the group consisting of O, N, S, Si, and P, and a fused ring group of a C$_3$-C$_{60}$ aliphatic ring and a C$_6$-C$_{60}$ aromatic ring.

When the ring formed by bonding between the above groups is an aryl(arylene) group, it may be preferably a C$_6$-C$_{18}$ aryl(arylene) group, more preferably a C$_6$-C$_{12}$ aryl(arylene) group, for example, benzene ring. Preferably, when neighboring R$^1$, R$^2$, or R$^3$ groups are linked to each other to form a benzene ring, naphthalene or phenanthrene can be formed together with benzene ring to which they are attached; when neighboring R$^4$ groups are linked to each other to form a benzene ring, benzoquinazoline, dibenzoquinazoline or the like can be formed together with quinazoline to which R$^4$ groups are attached; when Ar$^1$ and R$^1$ are linked to each other to form a ring, a heterocyclic group containing N, for example, carbazole derivatives, can be formed; when Ar$^2$ and R$^4$ are linked to each other to form a ring, a heterocyclic group containing N may be formed together with quinazoline to which they are attached; and when R$^1$ and R$^2$ and/or R$^2$ and R$^3$ are linked to each other to form an aromatic ring, fluorene derivatives, a heterocyclic group containing S, O or N, or the like, phenanthrene, fluorene, carbazole, dibenzothiophene, dibenzofuran, and the like may be formed together with benzene to which they are attached.

a and c are each an integer of 0 to 5, b is an integer of 0 to 3, d is an integer of 0 to 4, and when each of a, b, c and d is an integer of 2 or more, each of the plurality of R$^1$s to the plurality of R$^4$s may be the same or different from each other.

L$^1$ and L' may be each independently selected from the group consisting of a single bond, a C$_6$-C$_{60}$ arylene group, a fluorenylene group, a fused ring group of a C$_3$-C$_{60}$ aliphatic ring and a C$_6$-C$_{60}$ aromatic ring, and a C$_2$-C$_{60}$ heterocyclic group containing at least one heteroatom selected from the group consisting of O, N, S, Si, and P.

When L$^1$ and L' are an arylene group, they may be preferably a C$_6$-C$_{30}$ arylene group, more preferably a C$_6$-C$_{12}$ arylene group, for example, phenyl, biphenyl, or the like; when L$^1$ and L' are a heterocyclic group, they may be preferably a C$_2$-C$_{30}$ heterocyclic group, more preferably a C$_2$-C$_{12}$ heterocyclic group, for example, dibenzofuran.

R$_a$ and R$_b$ may be each independently selected from the group consisting of a C$_6$-C$_{60}$ aryl group, a fluorenyl group, a fused ring group of a C$_3$-C$_{60}$ aliphatic ring and a C$_6$-C$_{60}$ aromatic ring, and a C$_2$-C$_{60}$ heterocyclic group containing at least one heteroatom selected from the group consisting of O, N, S, Si, and P.

R$^5$ to R$^{11}$ may be each independently selected from the group consisting of hydrogen, halogen, a C$_1$-C$_{50}$ alkyl group, a C$_2$-C$_{20}$ alkenyl group, a C$_2$-C$_{20}$ alkynyl group, a C$_1$-C$_{30}$ alkoxyl group, a C$_6$-C$_{60}$ aryl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, and a C$_3$-C$_{50}$ alkylacetate group.

The above aryl group, arylene group, fluorenyl group, fluorenylene group, heterocyclic group, fused ring group, alkyl group, alkenyl group, alkynyl group, alkoxyl group, aryloxyl group, alkylacetate group and a ring formed by linking between neighboring R$^1$ groups, neighboring R$^2$ groups, neighboring R$^3$ groups, neighboring R$^4$ groups, Ar$^1$ and R$^1$, Ar$^1$ and R$^2$, Ar$^2$ and R$^4$, R$^1$ and R$^2$, and R$^2$ and R$^3$ may be each optionally further substituted with one or more substituents selected from the group consisting of deuterium, halogen, a silane group, a siloxane group, a boron group, a germanium group, a cyano group, a nitro group, a C$_1$-C$_{20}$ alkylthio group, a C$_1$-C$_{20}$ alkoxyl group, a C$_1$-C$_{20}$ alkyl group, a C$_2$-C$_{20}$ alkenyl group, a C$_2$-C$_{20}$ alkynyl group, a C$_6$-C$_{20}$ aryl group, a C$_6$-C$_{20}$ aryl group substituted with deuterium, a fluorenyl group, a C$_2$-C$_{20}$ heterocyclic group containing at least one heteroatom selected from the group consisting of O, N, S, Si, and P, a C$_3$-C$_{20}$ cycloalkyl group, a C$_7$-C$_{20}$ arylalkyl group and a C$_8$-C$_{20}$ arylalkenyl group.

The above Formula 1 may be represented by one of the following Formulas 2 to 6.

<Formula 2>

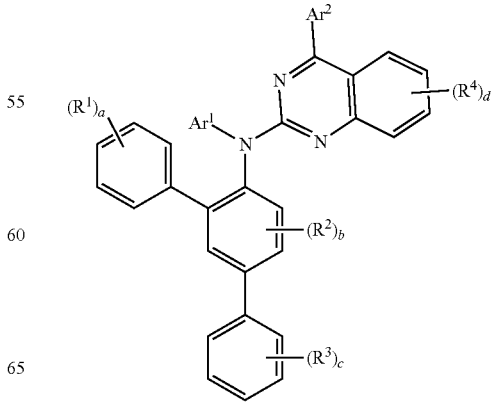

<Formula 3>

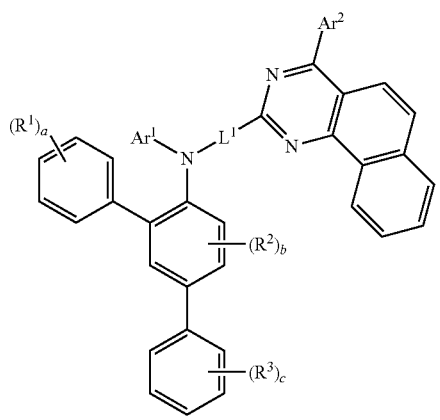

<Formula 4>

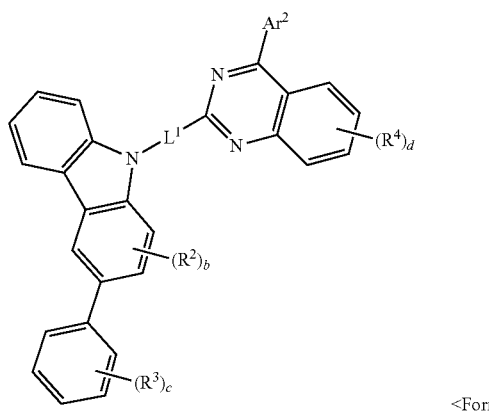

<Formula 5>

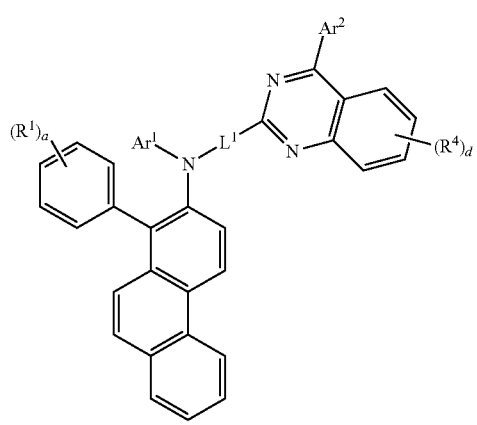

<Formula 6>

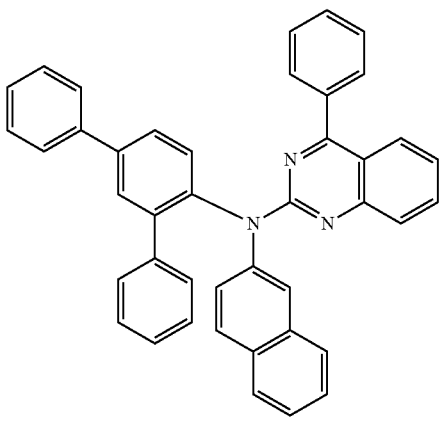

In the formulas 2 to 6, $Ar^1$, $Ar^2$, $R^1$ to $R^4$, a, b, c and d are the same as defined for the formula 1.

X may be selected from the group consisting of O, S, $N(R^{12})$ and $C(R^{13})(R^{14})$.

$R^{12}$ to $R^{14}$ may be each independently selected from the group consisting of hydrogen, halogen, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, and a $C_3$-$C_{50}$ alkylacetate group. In addition, $R^{13}$ and $R^{14}$ groups are optionally linked to each other to form a ring, as a result, a spiro compound may be formed.

Specifically, the compound represented by the Formula 1 may be one of the following compounds.

1-1

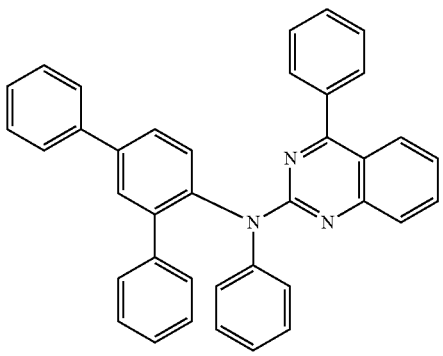

1-2

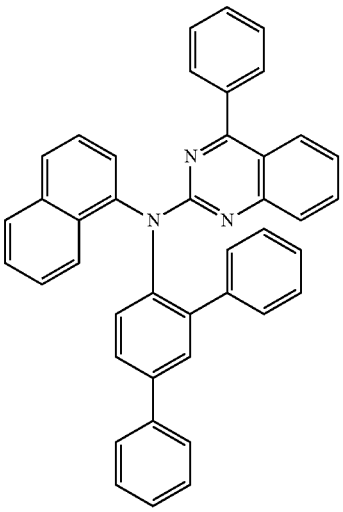

1-3

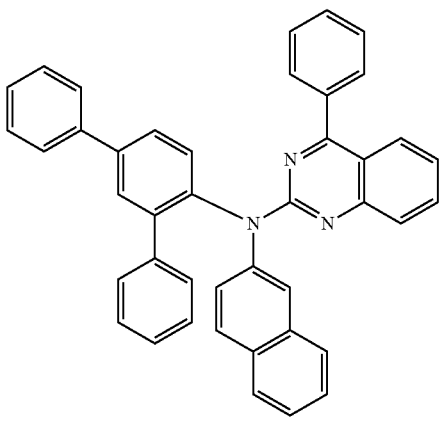

1-4
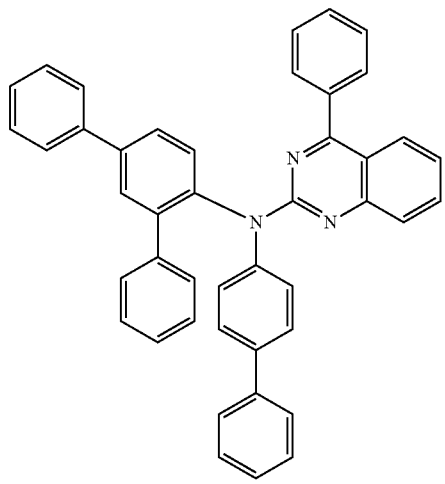
1-5
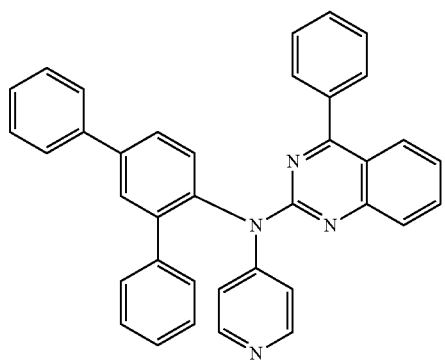
1-6
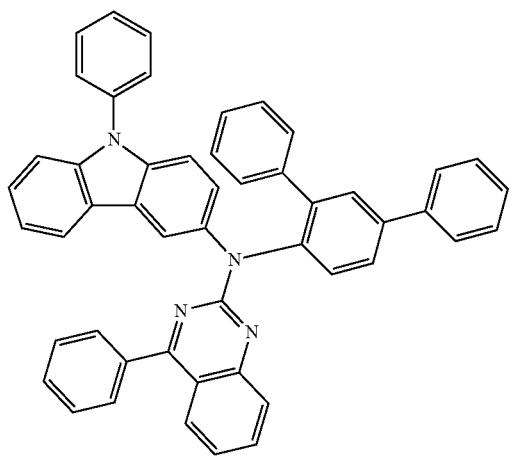
1-7
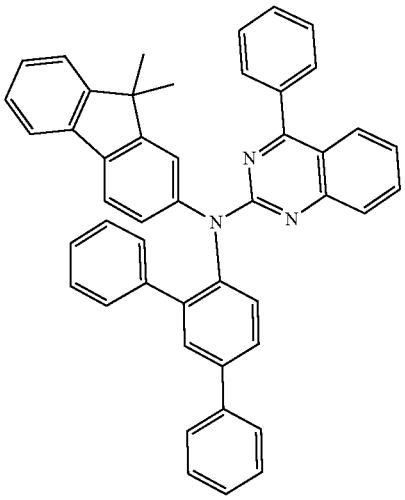
1-8
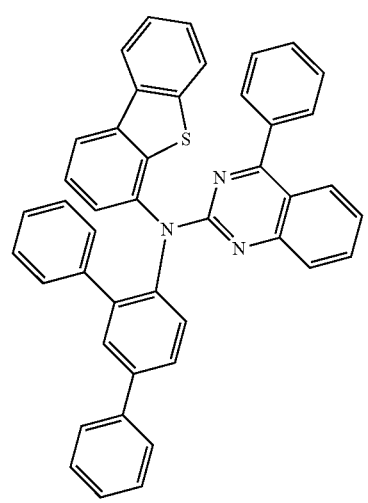
1-9
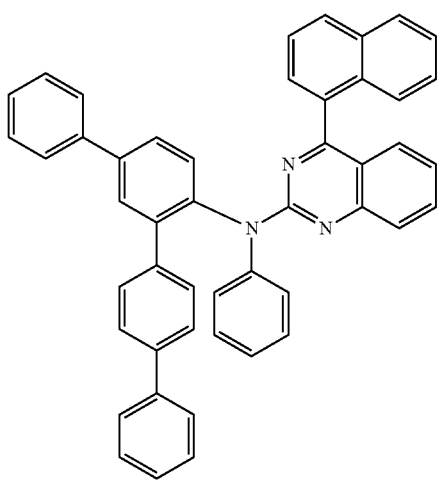

1-10
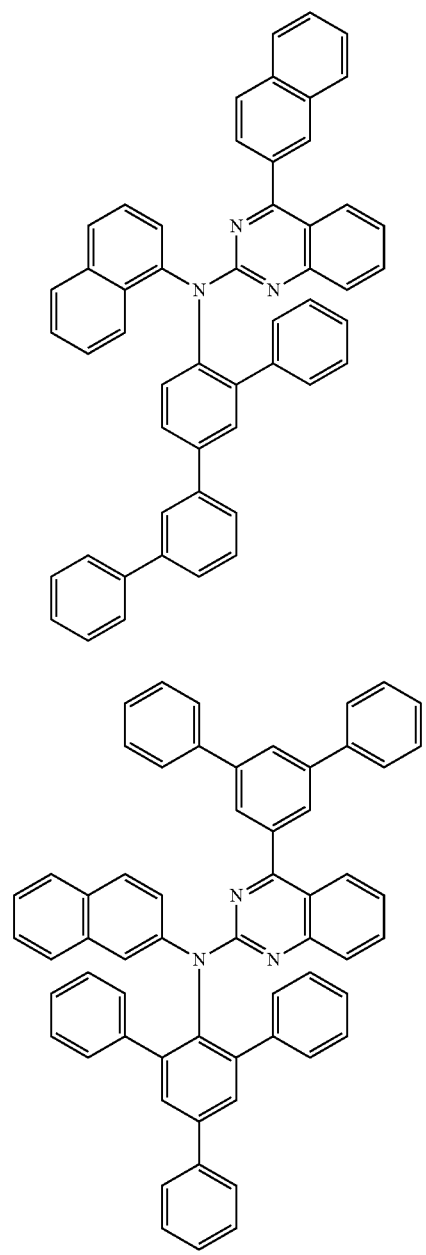
1-11
1-12
1-13
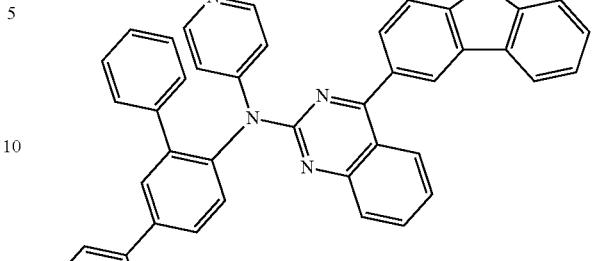
1-14
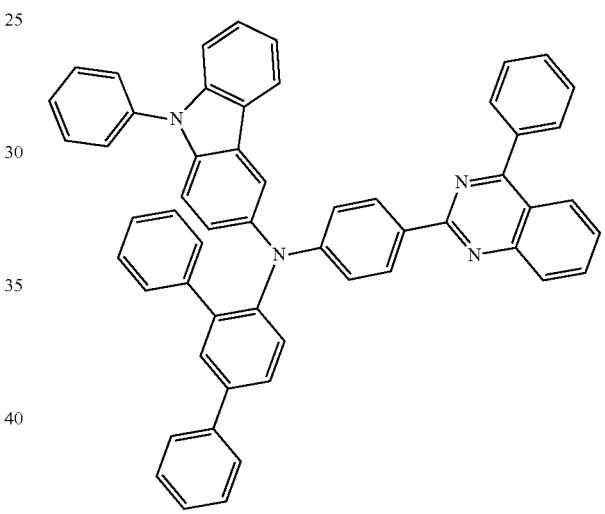
1-15
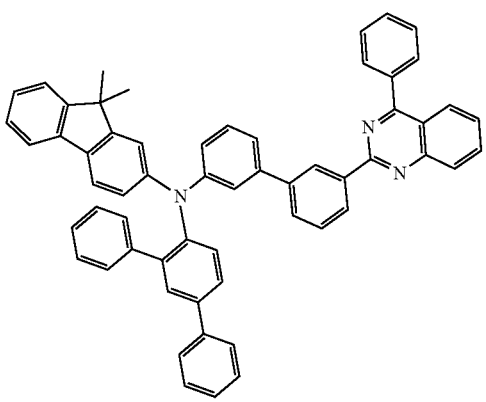

1-16
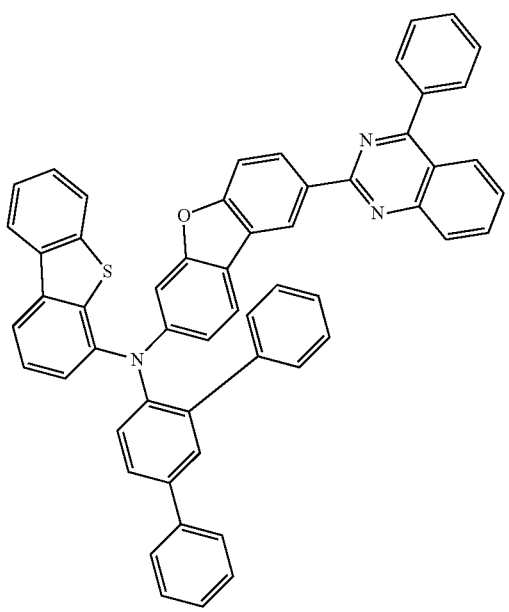
2-1
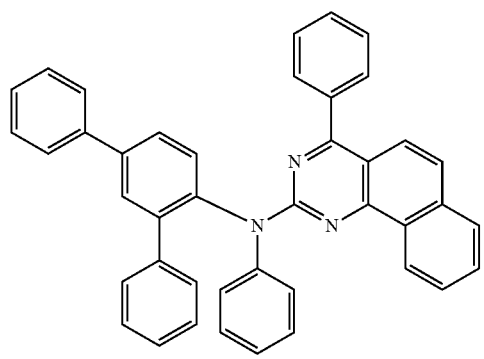
2-2
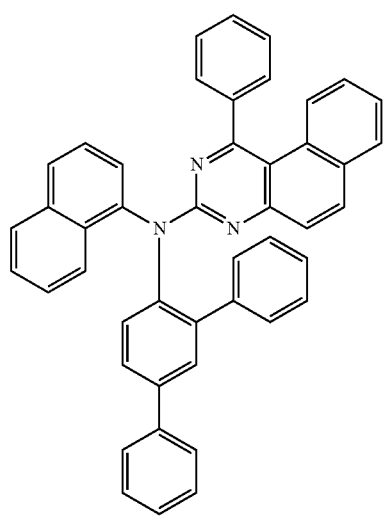
2-3
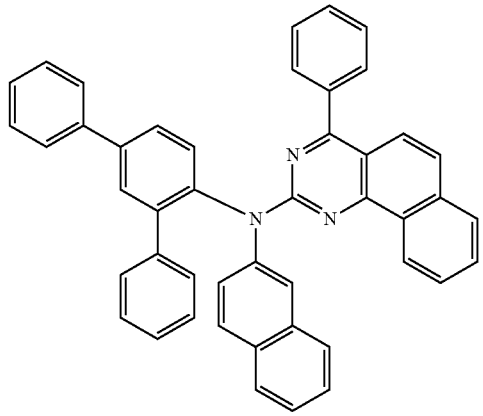
2-4
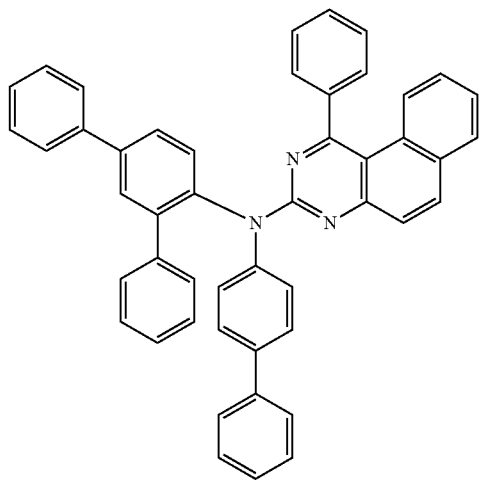
2-5
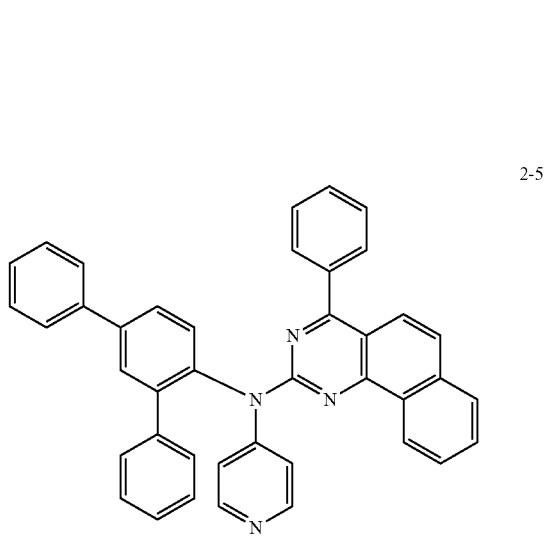

2-6
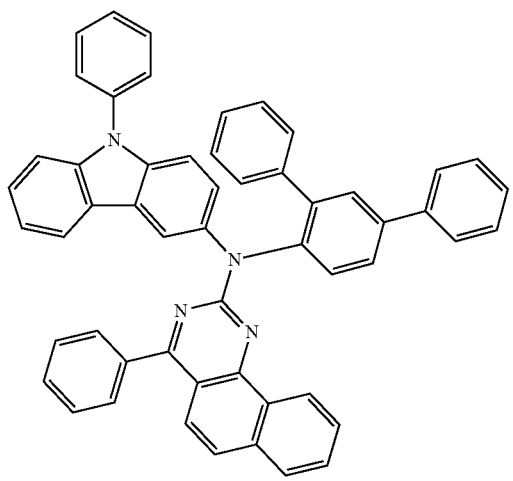
2-9
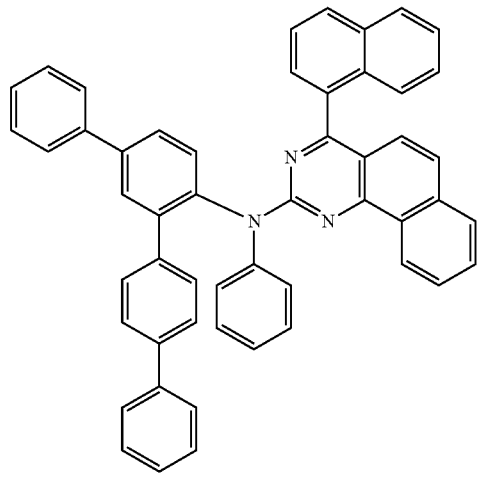
2-7
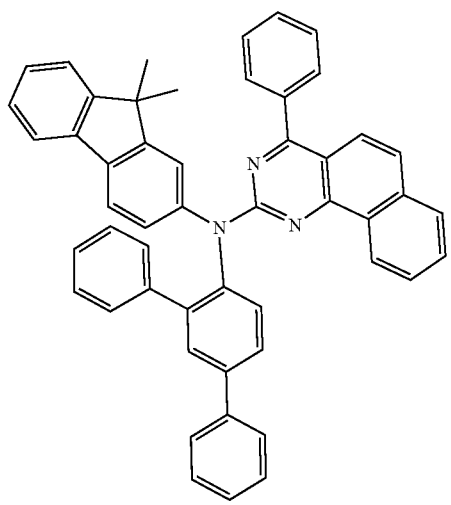
2-8
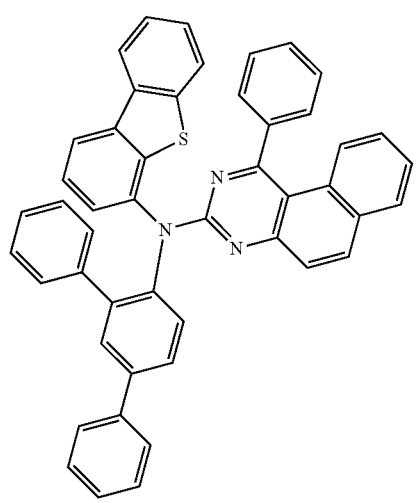
2-10
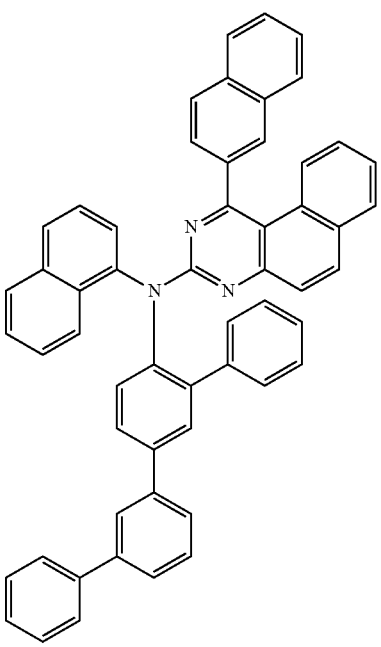

-continued
2-11
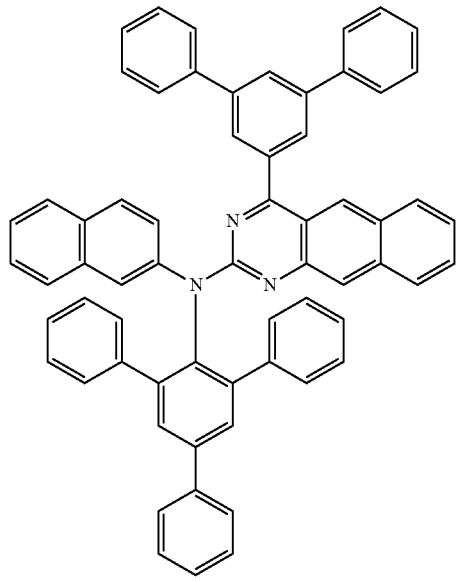
2-12
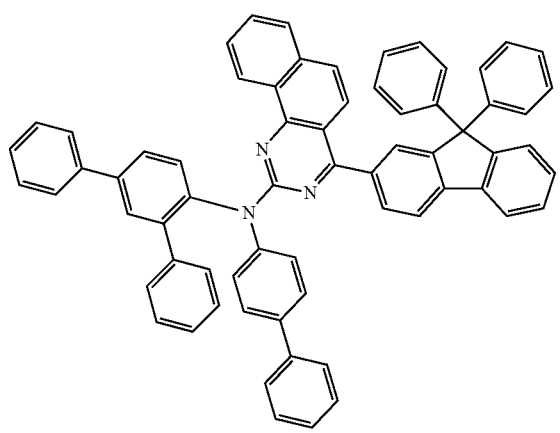
2-13
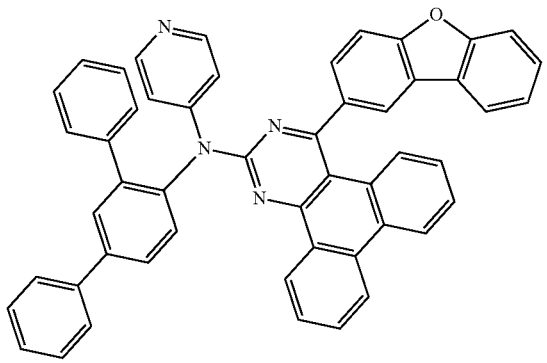
2-14
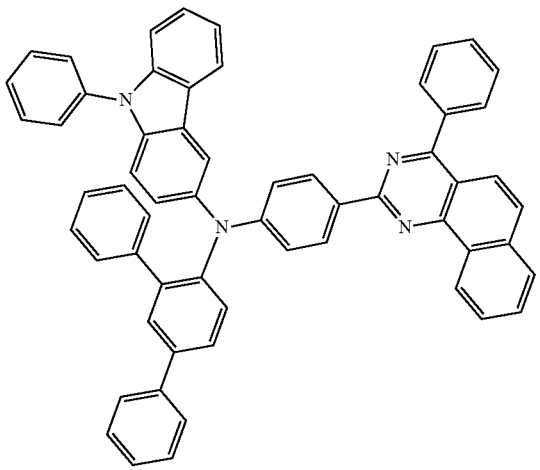
2-15
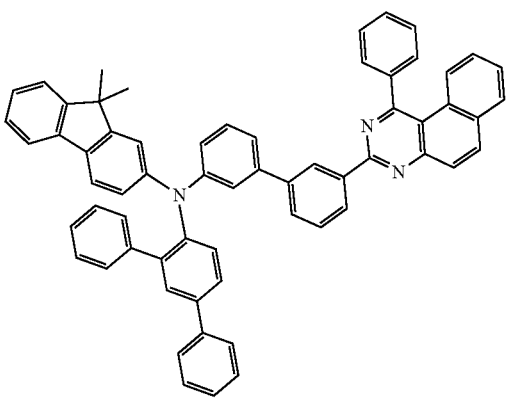
2-16
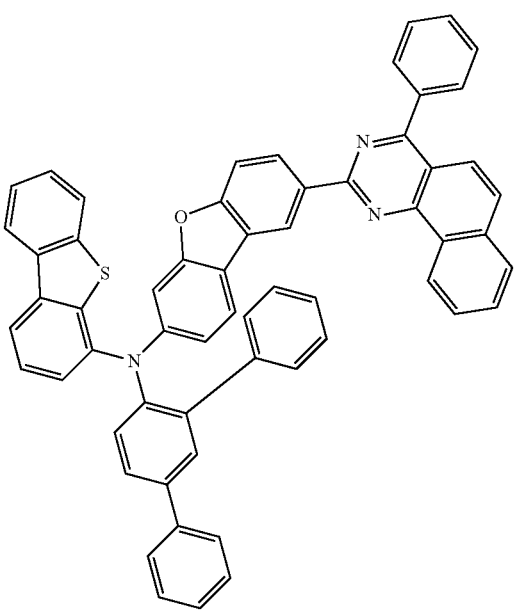

-continued
3-1
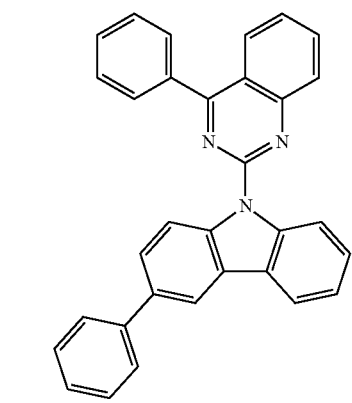
3-2
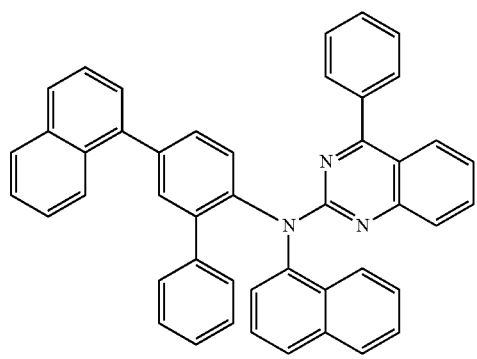
3-3
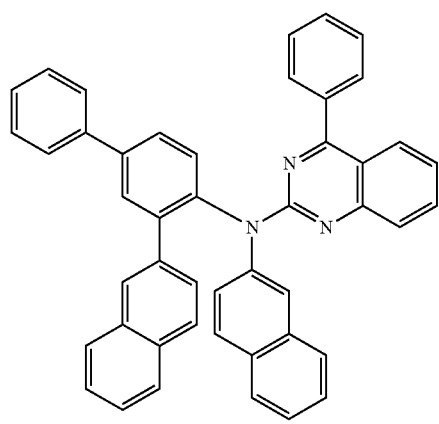
3-4
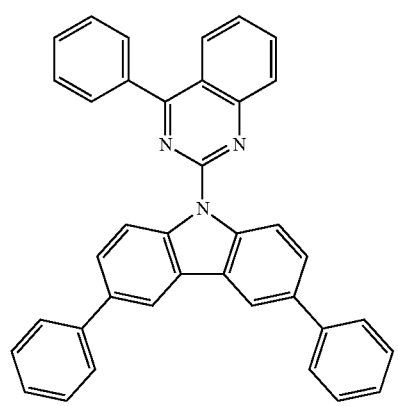
-continued
3-5
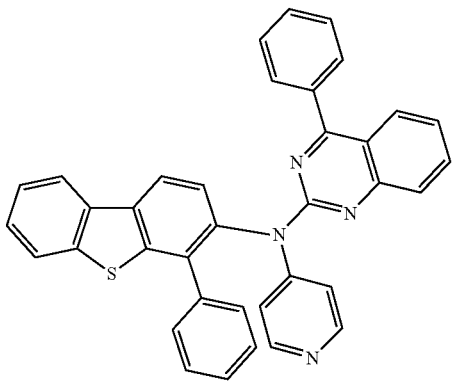
3-6
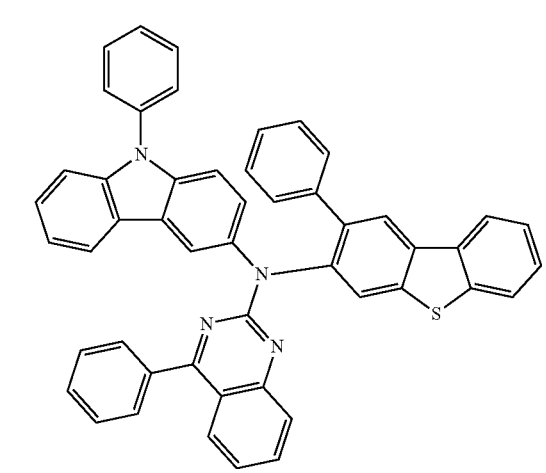
3-7
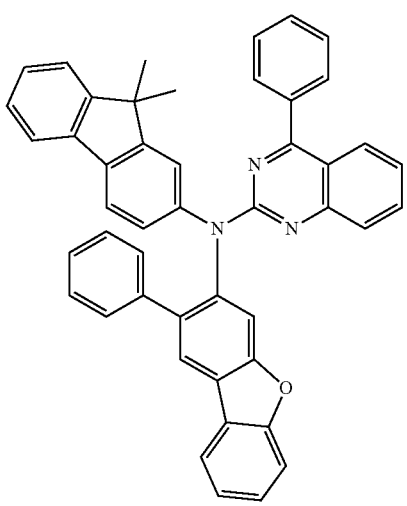

3-8
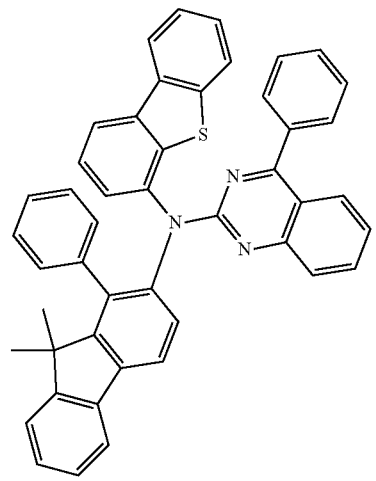
3-9
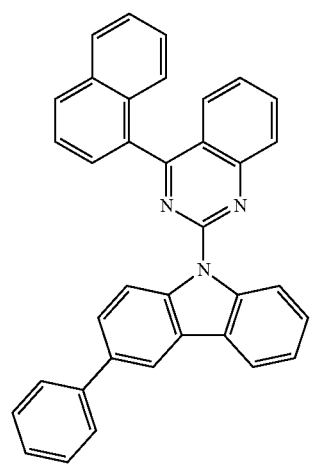
3-10
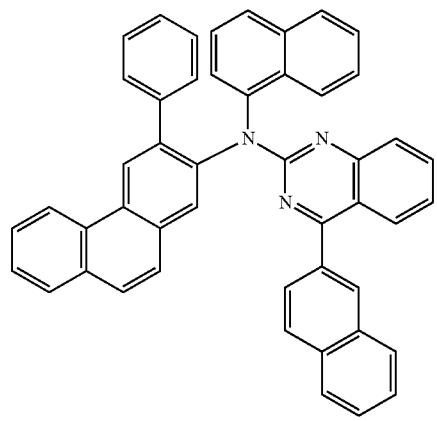
3-11
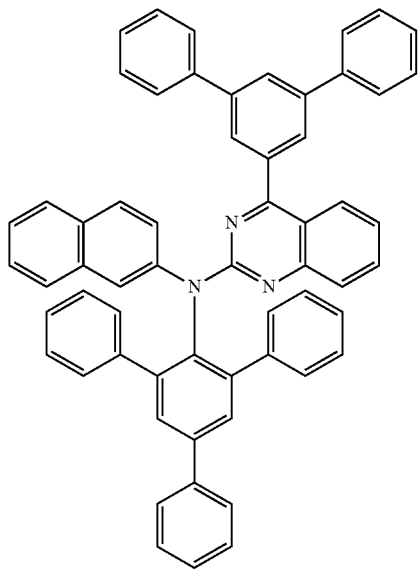
3-12
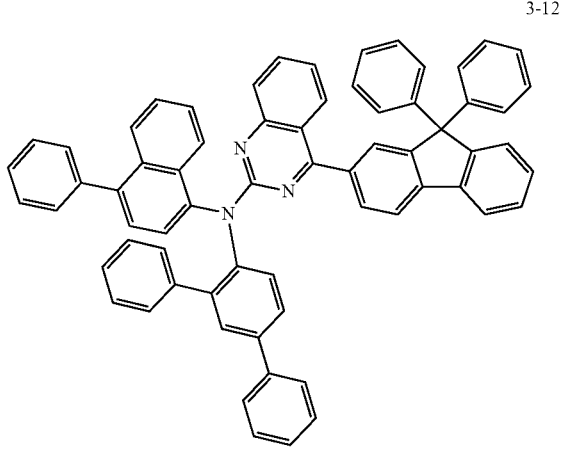
3-13
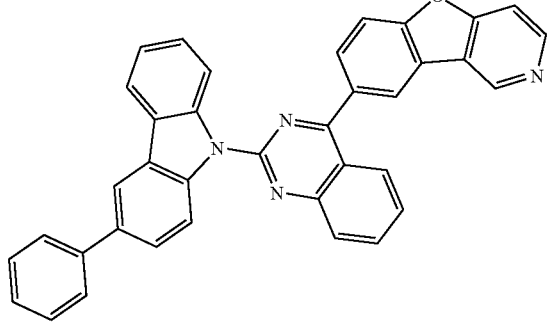

3-14
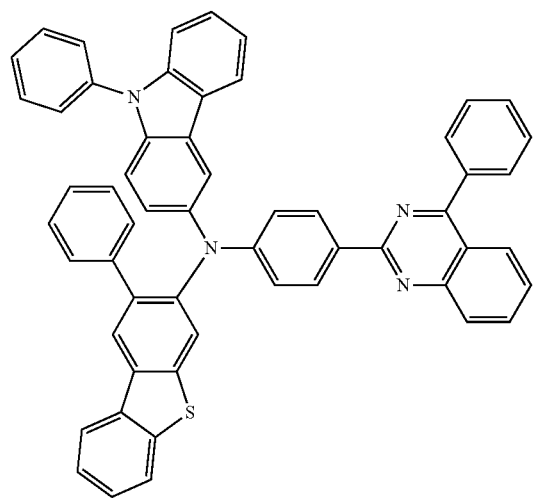
3-15
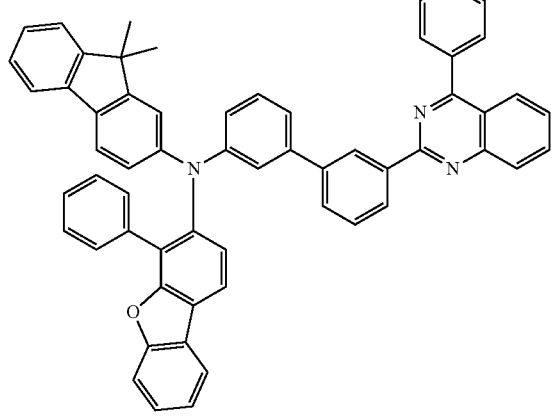
3-16
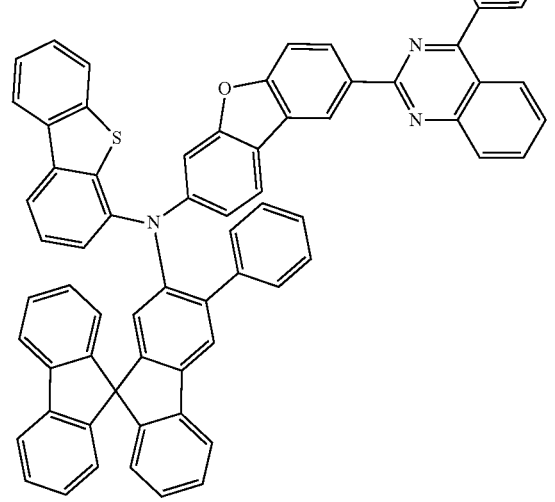
4-1
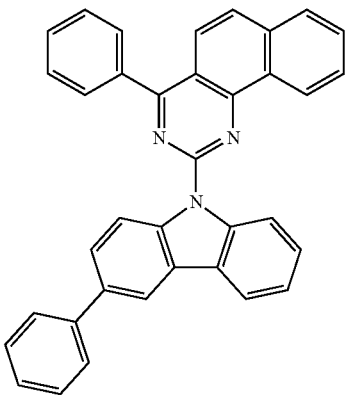
4-2
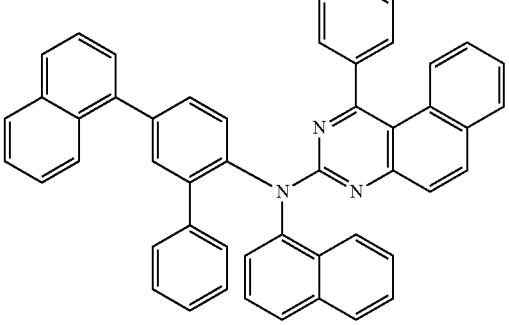
4-3
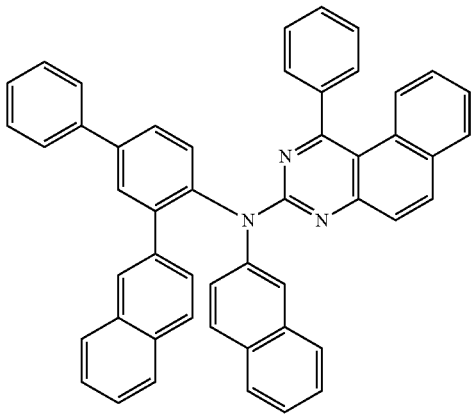
4-4
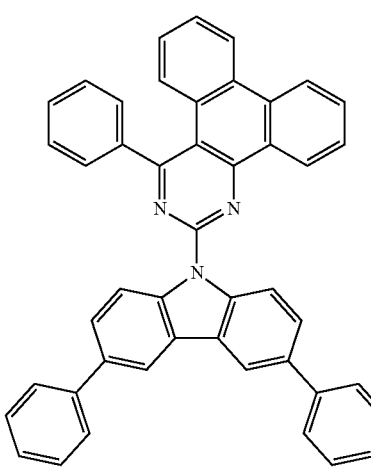

4-5
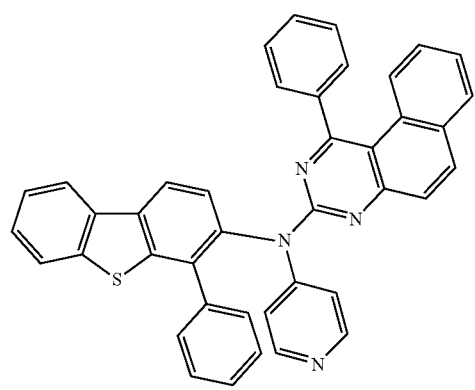
4-6
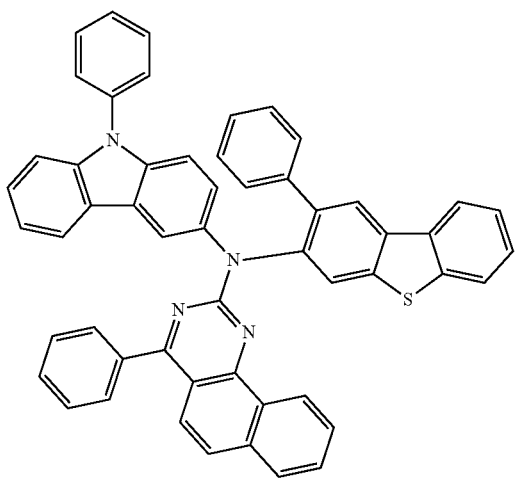
4-7
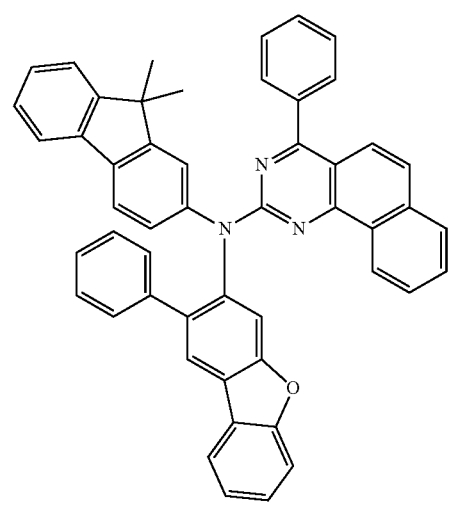
4-8
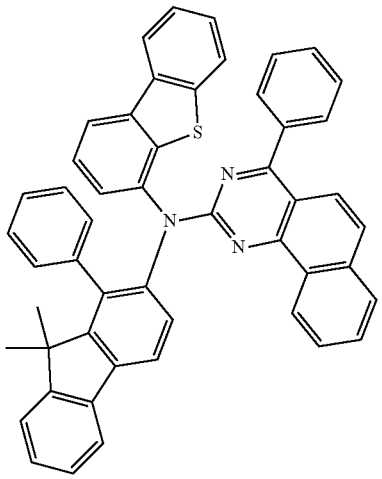
4-9
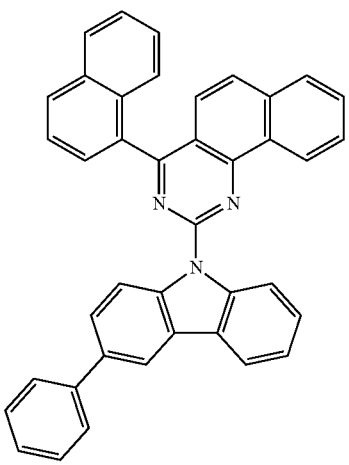
4-10
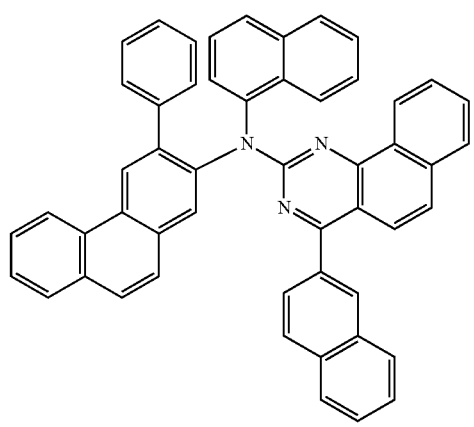

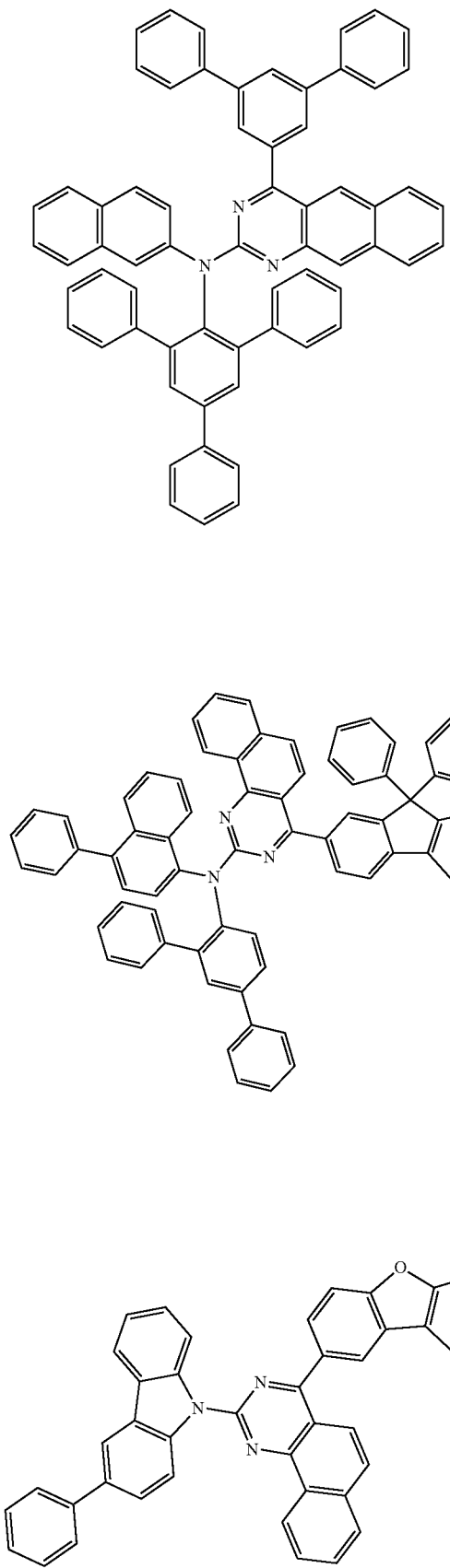
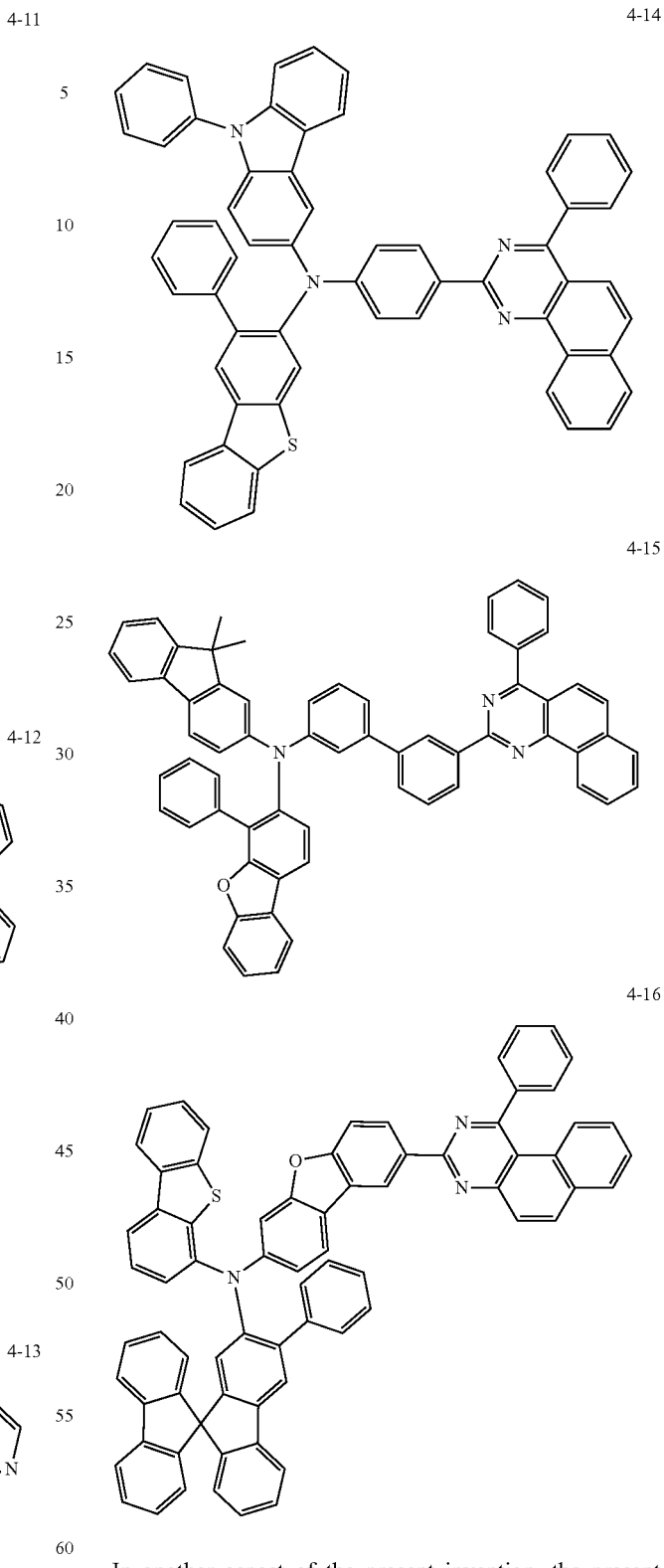
In another aspect of the present invention, the present invention provides compound for an organic electric element.
In another aspect of the present invention, the present invention provides an organic electric element comprising the compound represented by the formula 1. Here, the organic electric element may comprise a first electrode, a second electrode, and an organic material layer formed between the first electrode and the second electrode, wherein the organic material layer may comprise the compound represented by the formula 1, the compound may be comprised in at least one layer of a hole injection layer, a hole transport layer, an emission-auxiliary layer and a light emitting layer, and the compound may be comprised as a single compound or the component of the mixture of two or more kinds. That is, the compound represented by the formula 1 may be used as material of a hole injection layer, a hole transport layer, an emission-auxiliary layer or a light emitting layer. Preferably, the compound represented by the formula 1 may be used as phosphorescent host material of the light emitting layer or as material of an emission-auxiliary layer.

In another aspect of the present invention, the present invention provides an organic electric element further comprising a layer for improving luminous efficiency formed on one side of the first electrode and/or one side of the second electrode, the side not facing the organic material layer.

Hereinafter, Synthesis method of the compound represented by Formula 1 and preparation method of an organic electric element according to one embodiment of the present invention will be described in detail by way of examples. However, the present invention is not limited to the following examples.

SYNTHESIS EXAMPLE

For example, as shown in Reaction Scheme 1 below, the compound (final products) according to the present invention can be synthesized by reacting Sub 1 with Sub 2, but there is no limitation thereto.

<Reaction Scheme 1>

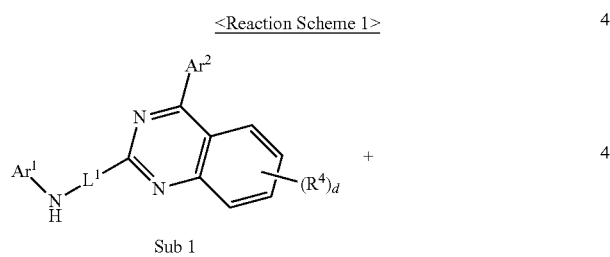

Sub 1

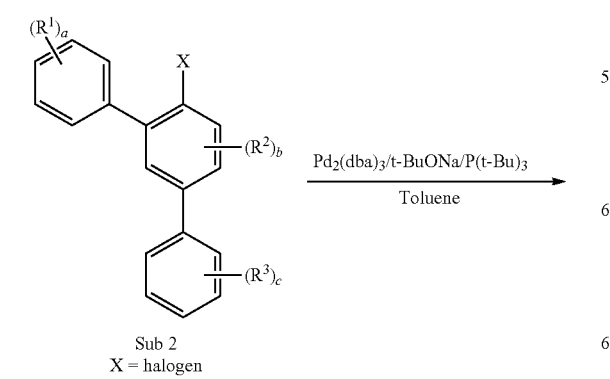

Sub 2
X = halogen

-continued

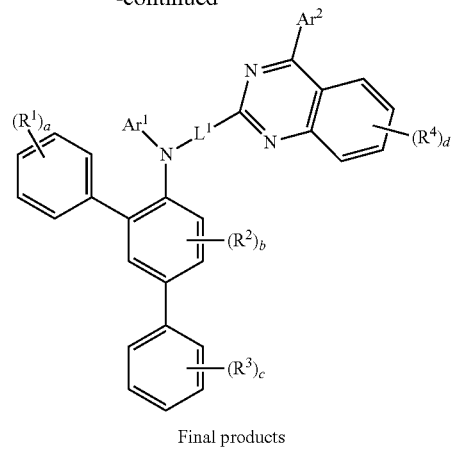

Final products

I. Synthesis Example of Sub 1

Sub 1 of the Reaction Scheme 1 can be synthesized according to the reaction route of the following Reaction Scheme 2, but there is no limitation thereto.

<Reaction Scheme 2>

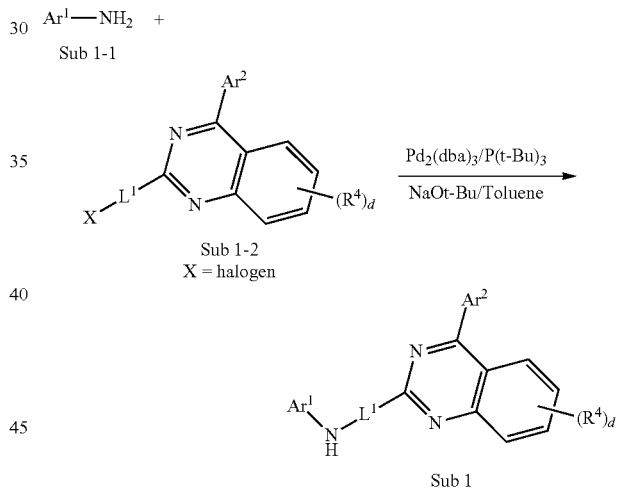

1. Synthesis Example of Sub 1(1)

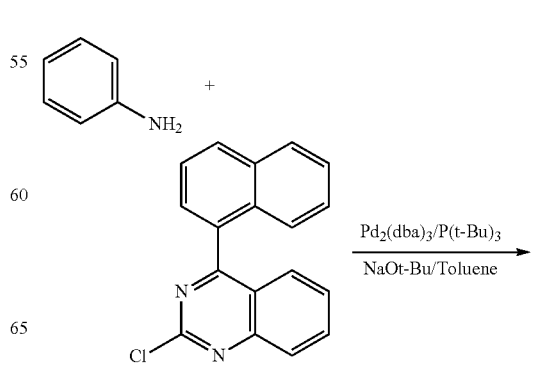

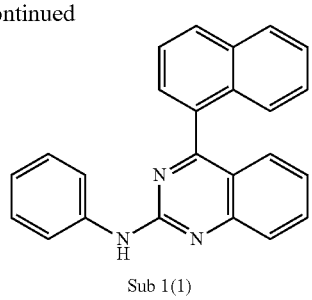

Sub 1(1)

After 2-chloro-4-(naphthalen-1-yl)quinazoline (7.0 g, 24 mmol) was dissolved in toluene, aniline (1.9 g, 20 mmol), Pd₂(dba)₃ (0.5 g, 0.6 mmol), P(t-Bu)₃ (0.2 g, 2 mmol), NaOt-Bu (5.8 g, 60 mmol) and toluene (300 mL) were added thereto. Then, the mixture was stirred under refluxing at 100□. When the reaction was completed, the resultant was extracted with ether and water. The organic layer was dried with MgSO₄ and concentrated. The concentrate was applied to silica gel column and recrystallized to obtain 6.3 g (yield: 75%) of the product.

2. Synthesis Example of Sub 1(6)

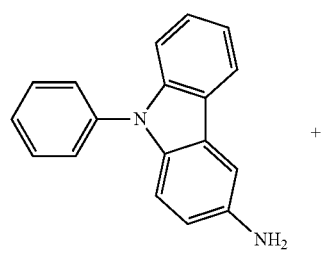

+

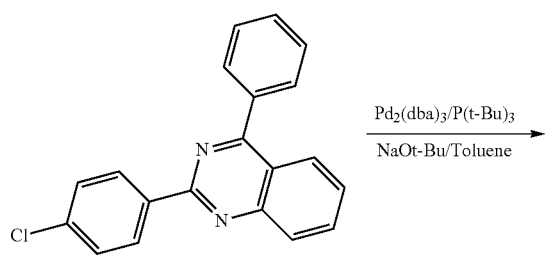

Sub 1(6)

2-(4-chlorophenyl)-4-phenylquinazoline (7.6 g, 24 mmol) and 9-phenyl-9H-carbazol-3-amine (5.2 g, 20 mmol) were reacted by the same method as in synthesis of Sub 1(1) to obtain 9.2 g (yield: 71%) of the product.

3. Synthesis Example of Sub 1(9)

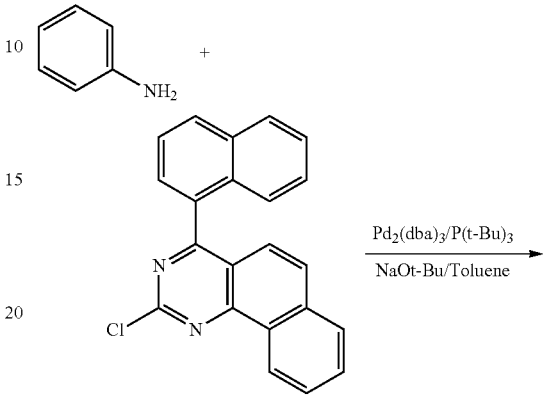

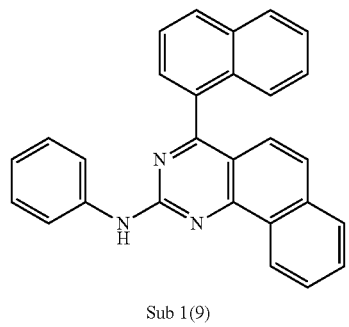

Sub 1(9)

2-(4-chlorophenyl)-4-phenylquinazoline (8.2 g, 24 mmol) and aniline (1.9 g, 20 mmol) were reacted by the same method as in synthesis of Sub 1(1) to obtain 7.1 g (yield: 74%) of the product.

The compound belonging to Sub 1 may be, but not limited to, the following compounds, and Table 1 shows FD-MS (Field Desorption-Mass Spectrometry) values of these.

Sub 1(1)

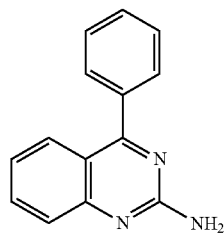

Sub 1(2)

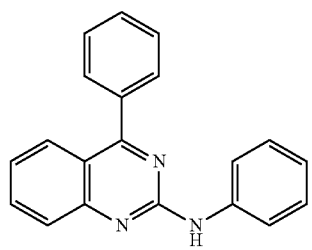

Sub 1(3)
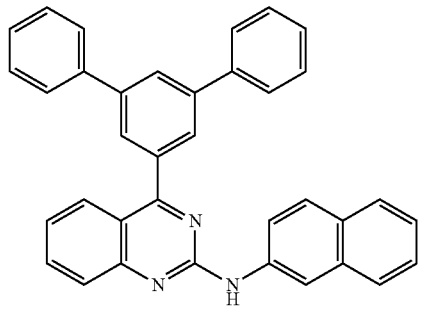
Sub 1(4)
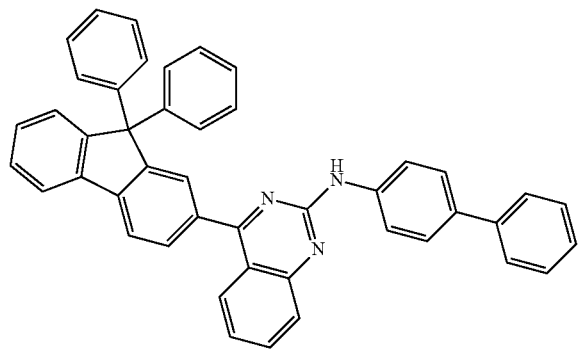
Sub 1(5)
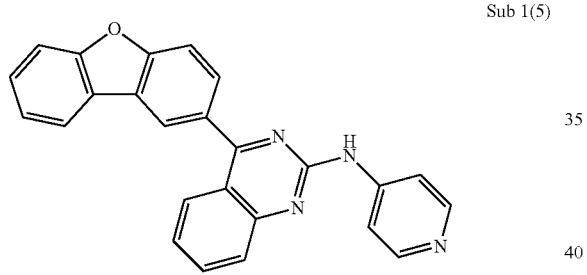
Sub 1(6)
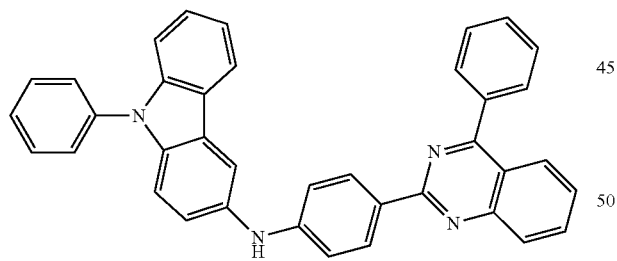
Sub 1(7)
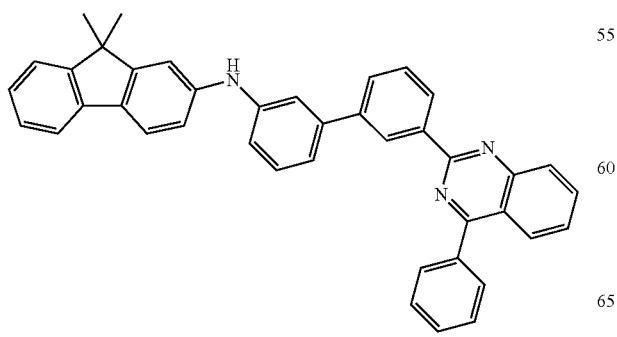
Sub 1(8)
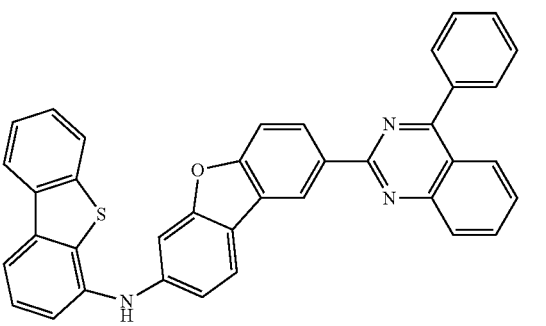
Sub 1(9)
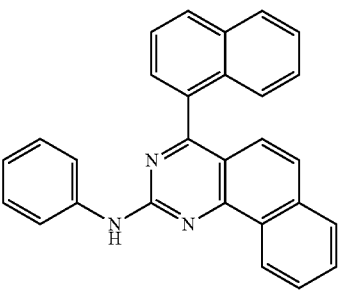
Sub 1(10)
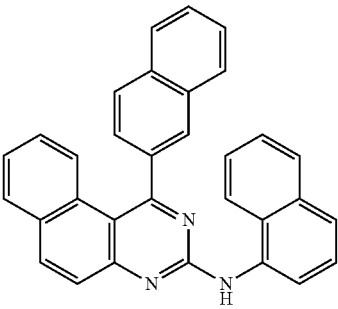
Sub 1(11)
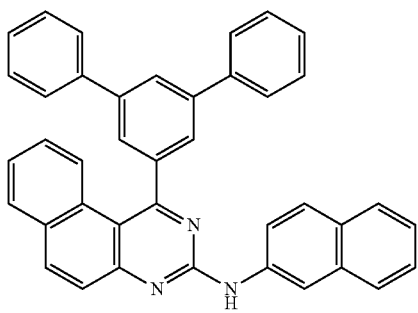

Sub 1(12)
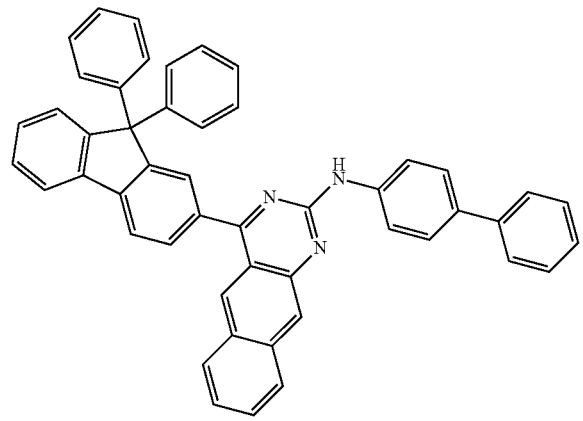
Sub 1(13)
Sub 1(14)
Sub 1(15)
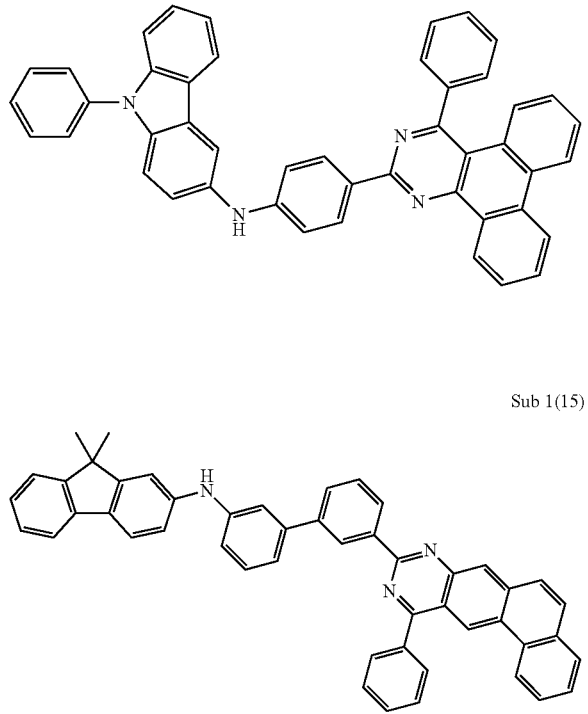
Sub 1(16)
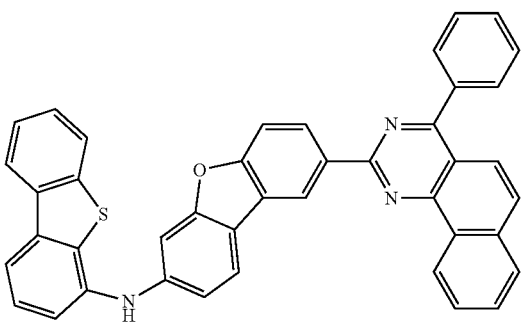
Sub 1(17)
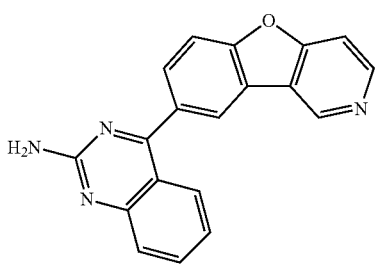
Sub 1(18)
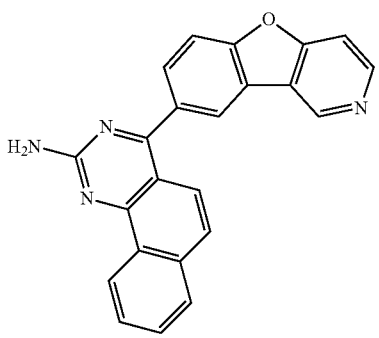
Sub 1(19)
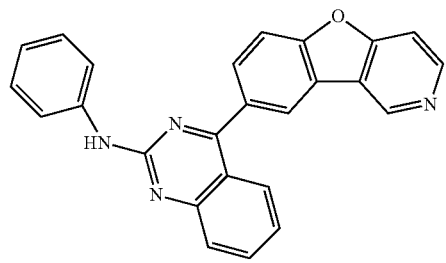
Sub 1(20)
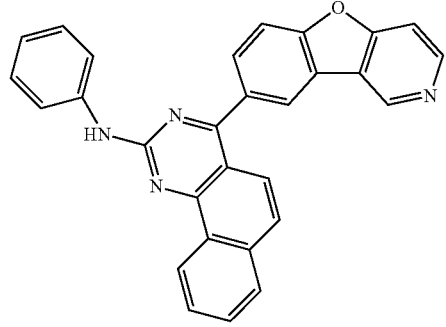

TABLE 1

| Compound | FD-MS | Compound | FD-MS |
|---|---|---|---|
| Sub 1(1) | m/z = 221.10($C_{14}H_{11}N_3$ = 221.26) | Sub 1(2) | m/z = 297.13($C_{20}H_{15}N_3$ = 297.36) |
| Sub 1(3) | m/z = 499.20($C_{36}H_{25}N_3$ = 499.62) | Sub 1(4) | m/z = 613.25($C_{45}H_{31}N_3$ = 613.76) |
| Sub 1(5) | m/z = 388.13($C_{25}H_{16}N_4O$ = 388.43) | Sub 1(6) | m/z = 538.22($C_{38}H_{26}N_4$ = 538.65) |
| Sub 1(7) | m/z = 565.25($C_{41}H_{31}N_3$ = 565.72) | Sub 1(8) | m/z = 569.16($C_{38}H_{23}N_3OS$ = 569.68) |
| Sub 1(9) | m/z = 397.16($C_{28}H_{19}N_3$ = 397.48) | Sub 1(10) | m/z = 447.17($C_{32}H_{21}N_3$ = 447.54) |
| Sub 1(11) | m/z = 549.22($C_{40}H_{27}N_3$ = 549.68) | Sub 1(12) | m/z = 663.27($C_{49}H_{33}N_3$ = 663.82) |
| Sub 1(13) | m/z = 488.16($C_{33}H_{20}N_4O$ = 488.55) | Sub 1(14) | m/z = 638.25($C_{46}H_{30}N_4$ = 638.77) |
| Sub 1(15) | m/z = 665.28($C_{49}H_{35}N_3$ = 665.84) | Sub 1(16) | m/z = 619.17($C_{42}H_{25}N_3OS$ = 619.74) |
| Sub 1(17) | m/z = 312.10($C_{19}H_{12}N_4O$ = 312.32) | Sub 1(18) | m/z = 362.12($C_{23}H_{14}N_4O$ = 362.38) |
| Sub 1(19) | m/z = 388.13($C_{25}H_{16}N_4O$ = 388.42) | Sub 1(20) | m/z = 438.15($C_{29}H_{18}N_4O$ = 438.48) |

II. Synthesis Example of Sub 2

1. Synthesis Example of Sub 2(8)

The following reaction scheme is an example of synthesis of a compound in which at least one of $R^1$ to $R^3$ in the compound Sub 2 of the above Reaction Scheme 1 forms a ring.

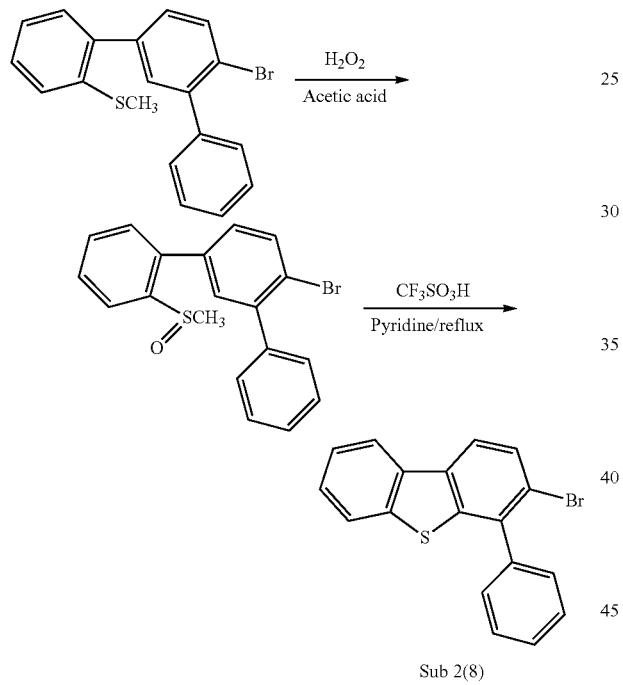

Sub 2(8)

4'-bromo-[1,1':3',1''-terphenyl]-2-yl)(methyl)sulfane (32.0 g, 0.09 mol) is dissolved in acetic acid and then hydrogen peroxide dissolved in acetic acid was added drop wise thereto. Then, the mixture was stirred at room temperature for 6 hours. When the reaction was completed, acetic acid was removed by the pressure reducer and then 26.7 g (yield: 80%) of 4'-bromo-[1,1':3',1''-terphenyl]-2-yl)(methyl)sulfane was obtained by using column chromatography. Then, 4'-bromo-[1,1':3',1''-terphenyl]-2-yl)(methyl)sulfane was added to an excess amount of trifluoromethanesulfonic acid and the mixture was stirred at room temperature for 24 hours. After adding water and pyridine (water:pyridine=8:1) slowly, followed by refluxing for 30 minutes. Then, after the temperature is lowered, the resultant was extracted with $CH_2Cl_2$ and washed with water. Then, small amount of water was removed with anhydrous $MgSO_4$, followed by filtering under reduced pressure. Then, the organic solvent was concentrated and the resulting product was separated by column chromatography to obtain 17.6 g (yield: 72%) of Sub 2 (8).

The compound belonging to Sub 2 may be, but not limited to, the following compounds, and Table 2 shows FD-MS (Field Desorption-Mass Spectrometry) values of these.

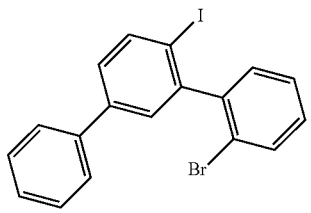

Sub 2(1)

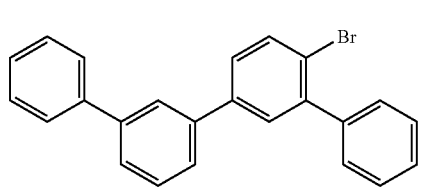

Sub 2(2)

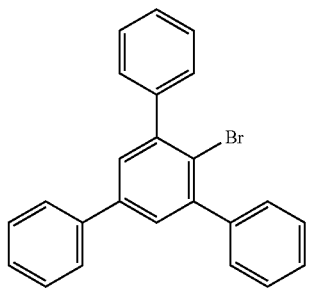

Sub 2(3)

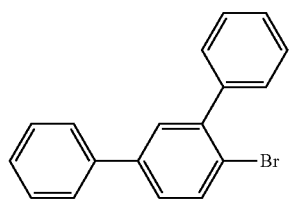

Sub 2(4)

Sub 2(5)
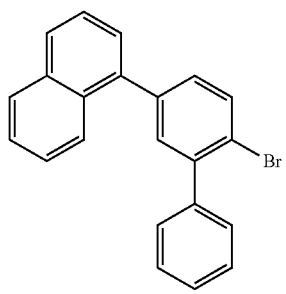
Sub 2(6)
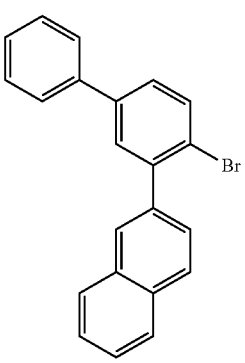
Sub 2(7)
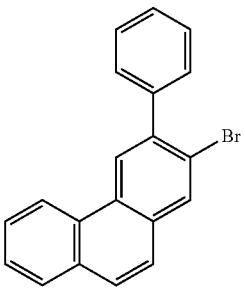
Sub 2(8)
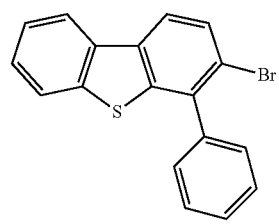
Sub 2(9)
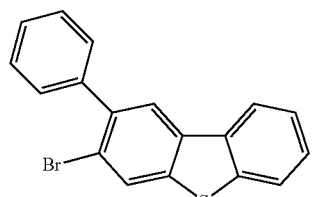
Sub 2(10)
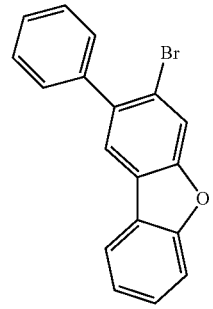
Sub 2(11)
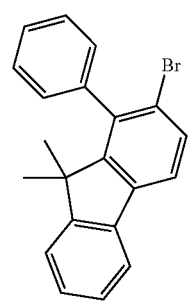
TABLE 2
| Compound | FD-MS | Compound | FD-MS |
| --- | --- | --- | --- |
| Sub 2(1) | m/z = 433.92($C_{18}H_{12}BrI$ = 435.10) | Sub 2(2) | m/z = 384.05($C_{24}H_{17}Br$ = 385.30) |
| Sub 2(3) | m/z = 384.05($C_{24}H_{17}Br$ = 385.30) | Sub 2(4) | m/z = 308.02($C_{18}H_{13}Br$ = 309.21) |
| Sub 2(5) | m/z = 358.04($C_{22}H_{15}Br$ = 359.27) | Sub 2(6) | m/z = 358.04($C_{22}H_{15}Br$ = 359.27) |
| Sub 2(7) | m/z = 332.02($C_{20}H_{13}Br$ = 333.23) | Sub 2(8) | m/z = 337.98($C_{18}H_{11}BrS$ = 339.25) |
| Sub 2(9) | m/z = 337.98($C_{18}H_{11}BrS$ = 339.25) | Sub 2(10) | m/z = 322.00($C_{18}H_{11}BrO$ = 323.19) |
| Sub 2(11) | m/z = 348.05($C_{21}H_{17}Br$ = 349.27) | | |

III. Synthesis Example of Final Products

1. Synthesis Example of 1-1

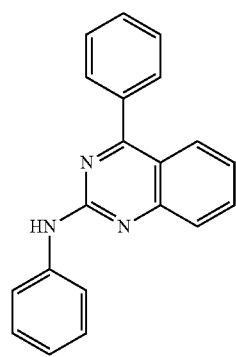

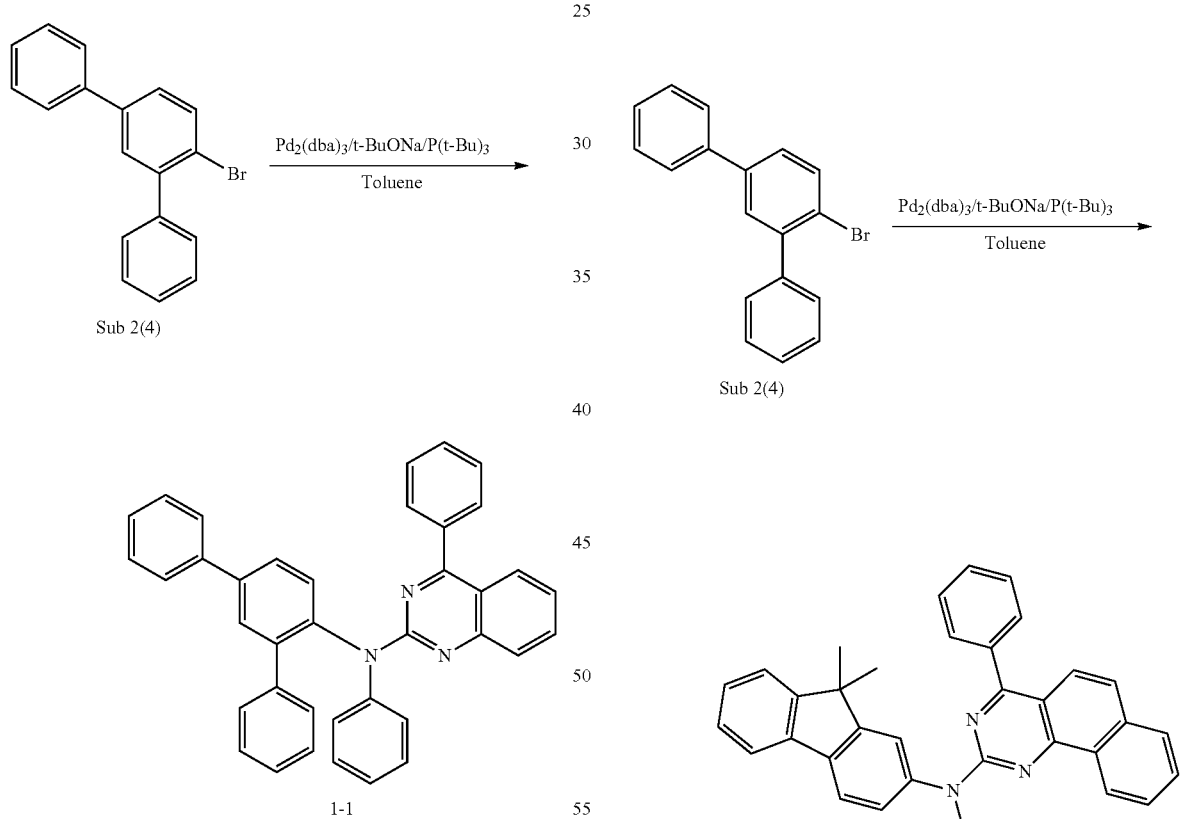

After Sub 1(2) (6.0 g, 20 mmol) was dissolved in toluene, Sub 2(4) (7.4 g, 24 mmol) was added and Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added thereto. Then, the mixture was stirred under refluxing at 100° C. for 24 hours. When the reaction was completed, the resultant was extracted with ether and water. The organic layer was dried with MgSO$_4$ and concentrated. The concentrate was applied to silica gel column and recrystallized to obtain 10.0 g (yield: 79%) of the product.

2. Synthesis Example of 2-7

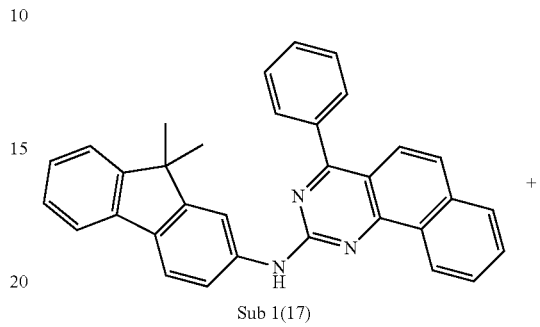

After Sub 1(17) (9.3 g, 20 mmol) was dissolved in toluene, Sub 2(4) (7.4 g, 24 mmol) was added thereto. Then, 13.0 g (yield: 78%) of the product was obtained by the same method as in synthesis of Sub 1-1.

3. Synthesis Example of 3-1

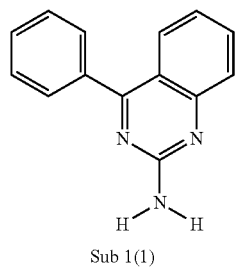
Sub 1(1)

+

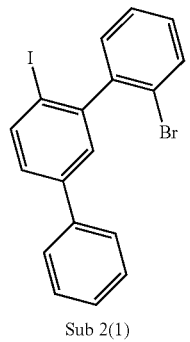
Sub 2(1)

$\xrightarrow{\text{Pd}_2(\text{dba})_3/\text{t-BuONa}/\text{P(t-Bu)}_3}_{\text{Toluene}}$

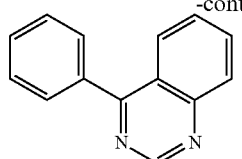

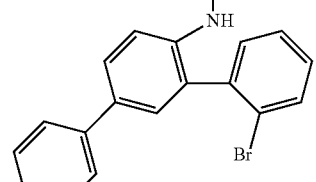
Sub Product $\xrightarrow{\text{Pd}_2(\text{dba})_3/\text{t-BuONa}/\text{P(t-Bu)}_3}_{\text{Toluene}}$

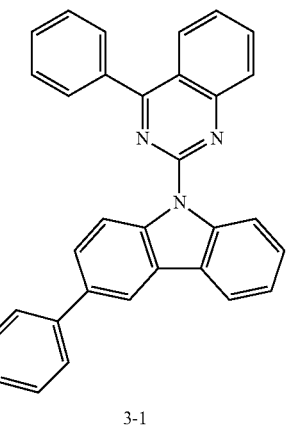
3-1

After Sub 1(1) (4.4 g, 20 mmol) was dissolved in toluene, Sub 2(1) (10.4 g, 24 mmol) was added thereto. Then, 9.0 g (yield: 71%) of the product was obtained by the same method as in synthesis of Sub 1-1. Unstable NH and Br of Sub Product was reacted once more to obtain 7.3 g (yield: 68%) of final compound 3-1.

The FD-MS values of some compounds of the present invention prepared according to the above synthesis examples are shown in Table 3 below.

TABLE 3

| Compound | FD-MS | Compound | FD-MS |
| --- | --- | --- | --- |
| 1-1 | m/z = 525.22($C_{38}H_{27}N_3$ = 525.66) | 1-2 | m/z = 575.24($C_{42}H_{29}N_3$ = 575.72) |
| 1-3 | m/z = 575.24($C_{42}H_{29}N_3$ = 575.72) | 1-4 | m/z = 601.25($C_{44}H_{31}N_3$ = 601.75) |
| 1-5 | m/z = 526.22($C_{37}H_{26}N_4$ = 526.64) | 1-6 | m/z = 690.28($C_{50}H_{34}N_4$ = 690.85) |
| 1-7 | m/z = 641.28($C_{47}H_{35}N_3$ = 641.82) | 1-8 | m/z = 631.21($C_{44}H_{29}N_3S$ = 631.80) |
| 1-9 | m/z = 651.27($C_{48}H_{33}N_3$ = 651.81) | 1-10 | m/z = 701.28($C_{52}H_{35}N_3$ = 701.87) |
| 1-11 | m/z = 803.33($C_{60}H_{41}N_3$ = 804.01) | 1-12 | m/z = 841.35($C_{63}H_{43}N_3$ = 842.06) |
| 1-13 | m/z = 616.23($C_{43}H_{28}N_4O$ = 616.72) | 1-14 | m/z = 766.31($C_{56}H_{38}N_4$ = 766.95) |
| 1-15 | m/z = 793.35($C_{59}H_{43}N_3$ = 794.01) | 1-16 | m/z = 797.25($C_{56}H_{35}N_3OS$ = 797.98) |
| 2-1 | m/z = 575.24($C_{42}H_{29}N_3$ = 575.72) | 2-2 | m/z = 625.25($C_{46}H_{31}N_3$ = 625.78) |
| 2-3 | m/z = 625.25($C_{46}H_{31}N_3$ = 625.78) | 2-4 | m/z = 651.27($C_{48}H_{33}N_3$ = 651.81) |
| 2-5 | m/z = 576.23($C_{41}H_{28}N_4$ = 576.70) | 2-6 | m/z = 740.29($C_{54}H_{36}N_4$ = 740.91) |
| 2-7 | m/z = 691.30($C_{51}H_{37}N_3$ = 691.88) | 2-8 | m/z = 681.22($C_{48}H_{31}N_3S$ = 681.86) |
| 2-9 | m/z = 701.28($C_{52}H_{35}N_3$ = 701.87) | 2-10 | m/z = 751.30($C_{56}H_{37}N_3$ = 751.93) |
| 2-11 | m/z = 853.35($C_{64}H_{43}N_3$ = 854.07) | 2-12 | m/z = 891.36($C_{67}H_{45}N_3$ = 892.12) |
| 2-13 | m/z = 716.26($C_{51}H_{32}N_4O$ = 716.84) | 2-14 | m/z = 816.33($C_{60}H_{40}N_4$ = 817.01) |
| 2-15 | m/z = 843.36($C_{63}H_{45}N_3$ = 844.07) | 2-16 | m/z = 847.27($C_{60}H_{37}N_3OS$ = 848.04) |
| 3-1 | m/z = 447.17($C_{32}H_{21}N_3$ = 447.54) | 3-2 | m/z = 625.25($C_{46}H_{31}N_3$ = 625.78) |
| 3-3 | m/z = 625.25($C_{46}H_{31}N_3$ = 625.78) | 3-4 | m/z = 523.20($C_{38}H_{25}N_3$ = 523.64) |
| 3-5 | m/z = 556.17($C_{37}H_{24}N_4S$ = 556.69) | 3-6 | m/z = 720.23($C_{50}H_{32}N_4S$ = 720.89) |
| 3-7 | m/z = 655.26($C_{47}H_{33}N_3O$ = 655.80) | 3-8 | m/z = 671.24($C_{47}H_{33}N_3S$ = 671.86) |
| 3-9 | m/z = 497.19($C_{36}H_{23}N_3$ = 497.60) | 3-10 | m/z = 649.25($C_{48}H_{31}N_3$ = 649.80) |
| 3-11 | m/z = 803.33($C_{60}H_{41}N_3$ = 804.01) | 3-12 | m/z = 891.36($C_{67}H_{45}N_3$ = 892.12) |
| 3-13 | m/z = 538.18($C_{37}H_{22}N_4O$ = 538.61) | 3-14 | m/z = 796.27($C_{56}H_{36}N_4S$ = 796.99) |
| 3-15 | m/z = 807.32($C_{59}H_{41}N_3O$ = 808.00) | 3-16 | m/z = 959.30($C_{69}H_{41}N_3OS$ = 960.17) |
| 4-1 | m/z = 497.19($C_{36}H_{23}N_3$ = 497.60) | 4-2 | m/z = 675.27($C_{50}H_{33}N_3$ = 675.84) |

TABLE 3-continued

| Compound | FD-MS | Compound | FD-MS |
|---|---|---|---|
| 4-3 | m/z = 675.27($C_{50}H_{33}N_3$ = 675.84) | 4-4 | m/z = 623.24($C_{46}H_{29}N_3$ = 623.76) |
| 4-5 | m/z = 606.19($C_{41}H_{26}N_4S$ = 606.75) | 4-6 | m/z = 770.25($C_{54}H_{34}N_4S$ = 770.95) |
| 4-7 | m/z = 705.28($C_{51}H_{35}N_3O$ = 705.86) | 4-8 | m/z = 721.26($C_{51}H_{35}N_3S$ = 721.92) |
| 4-9 | m/z = 547.20($C_{40}H_{25}N_3$ = 547.66) | 4-10 | m/z = 699.27($C_{52}H_{33}N_3$ = 699.86) |
| 4-11 | m/z = 853.35($C_{64}H_{43}N_3$ = 854.07) | 4-12 | m/z = 941.38($C_{71}H_{47}N_3$ = 942.18) |
| 4-13 | m/z = 588.20($C_{41}H_{24}N_4O$ = 588.67) | 4-14 | m/z = 846.28($C_{60}H_{38}N_4S$ = 847.05) |
| 4-15 | m/z = 857.34($C_{63}H_{43}N_3O$ = 858.06) | 4-16 | m/z = 1009.31($C_{73}H_{43}N_3OS$ = 1010.23) |

Fabrication and Evaluation of Organic Electronic Element

[Example 1] Blue OLED (an Emission-Auxiliary Layer)

ITO layer (anode) was formed on a glass substrate, and then $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine (hereinafter, "NPB") was vacuum-deposited with a thickness of 60 nm on the hole injection layer to form a hole transport layer. Subsequently, a film of the compound 1-1 of the present invention was vacuum-deposited on the hole transport layer to form a emission-auxiliary layer with a thickness of 20 nm. A light emitting layer with a thickness of 30 nm was deposited on the emission-auxiliary layer by using the 9,10-di(2-naphthyl)anthracene as a host material and BD-052X (made by Idemitsu kosan) as a dopant material in a weight ratio of 96:4.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "$Alq_3$") was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 31] Blue OLED (an Emission-Auxiliary Layer)

The OLEDs were fabricated in the same manner as described in Example 1 except that the compounds of the present invention described in Table 4, instead of the compound 1-1 according to one embodiment of the present invention, were used as an emission-auxiliary layer material.

Comparative Example 1

The OLED was fabricated in the same manner as described in Example 1 except that an emission-auxiliary layer was not formed.

[Comparative Example 2] to [Comparative Example 5]

The OLEDs were fabricated in the same manner as described in Example 1 except that one of the Comparative compounds A to D, instead of the compound 1-1 according to one embodiment of the present invention, was used as an emission-auxiliary layer material.

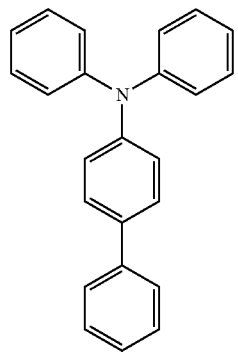

<Comp.compd A>

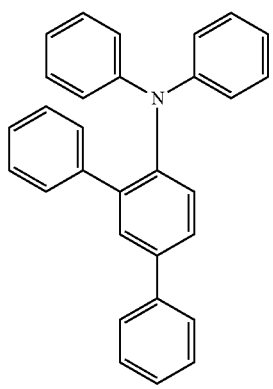

<Comp.compd B>

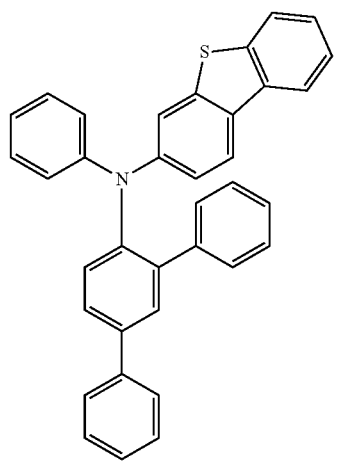

<Comp.compd C>

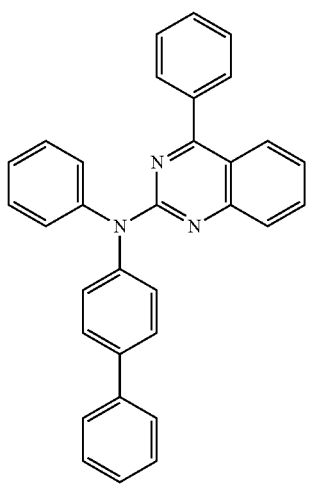

<Comp.compd D>

Electroluminescence (EL) characteristics were measured with a PR-650 (Photoresearch) by applying a forward bias DC voltage to the OLEDs prepared in Examples 1 to 31 of the present invention and Comparative Examples 1 to 5. And, the T95 life time was measured using a life time measuring apparatus manufactured by Macscience Inc. at reference brightness of 500 cd/m². The measurement results are shown in Table 4 below.

From the results shown in Table 4 above, it can be seen that OLEDs using the compound of the present invention as an emission-auxiliary layer material showed a lower driving voltage and the improved luminous efficiency and lifetime than OLED not comprising an emission-auxiliary layer or OLED using Comparative Compounds A to D as an emission-auxiliary layer material.

That is, the results of Comparative Examples 2 to 5 and Examples 1 to 31 in which the an emission-auxiliary layer was formed were superior to those of Comparative Example 1 in which an emission-auxiliary was not formed, and the results of Comparative Examples 3 and 4 were better than those of Comparative Examples 1 and 2, wherein Comparative Examples 1 and 2 use a comparative compounds A and B, respectively, in which the tertiary amine is substituted with only the general aryl group, and Comparative Examples 3 and 4 use a Comparative compounds C and D, respectively, in which a tertiary amine is substituted with a heteroaryl group such as dibenzothiophen or quinazoline, and the results of Examples 1 to 31 using the compound of the present invention in which a specific aryl group and quinazoline are substituted are more excellent than all Comparative Examples.

Such device results may be attributed to the form of the substituents shown in the compounds of the present invention.

First, it is thanks to a feature of terphenyl substituents substituted with ortho and para positions. This can be seen

TABLE 4

| | Compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex(1) | — | 5.9 | 16.1 | 500.0 | 3.1 | 51.8 | |
| comp. Ex(2) | comp. Com A | 6.0 | 11.9 | 500.0 | 4.2 | 60.2 | (0.15, 0.13) |
| comp. Ex(3) | comp. Com B | 5.8 | 10.2 | 500.0 | 4.9 | 63.5 | (0.14, 0.14) |
| comp. Ex(4) | comp. Com C | 5.7 | 9.4 | 500.0 | 5.3 | 65.6 | (0.15, 0.14) |
| comp. Ex(5) | comp. Com D | 5.5 | 9.6 | 500.0 | 5.2 | 64.1 | (0.14, 0.14) |
| Ex.(1) | Com.(1-1) | 4.9 | 7.9 | 500.0 | 6.4 | 106.0 | (0.14, 0.14) |
| Ex.(2) | Com.(1-2) | 5.0 | 7.9 | 500.0 | 6.3 | 102.7 | (0.15, 0.13) |
| Ex.(3) | Com.(1-3) | 5.0 | 7.9 | 500.0 | 6.3 | 104.4 | (0.15, 0.16) |
| Ex.(4) | Com.(1-4) | 4.9 | 7.7 | 500.0 | 6.5 | 109.4 | (0.15, 0.14) |
| Ex.(5) | Com.(1-5) | 4.9 | 7.9 | 500.0 | 6.3 | 102.5 | (0.15, 0.13) |
| Ex.(6) | Com.(1-6) | 4.9 | 7.8 | 500.0 | 6.4 | 101.4 | (0.14, 0.14) |
| Ex.(7) | Com.(1-7) | 4.9 | 7.9 | 500.0 | 6.3 | 101.6 | (0.15, 0.14) |
| Ex.(8) | Com.(1-8) | 4.8 | 7.7 | 500.0 | 6.5 | 106.9 | (0.15, 0.13) |
| Ex.(9) | Com.(1-9) | 4.8 | 7.9 | 500.0 | 6.3 | 109.6 | (0.15, 0.14) |
| Ex.(10) | Com.(1-10) | 4.9 | 7.7 | 500.0 | 6.5 | 110.0 | (0.15, 0.13) |
| Ex.(11) | Com.(1-11) | 4.9 | 7.7 | 500.0 | 6.5 | 108.7 | (0.14, 0.14) |
| Ex.(12) | Com.(1-12) | 5.0 | 7.7 | 500.0 | 6.5 | 100.3 | (0.14, 0.14) |
| Ex.(13) | Com.(1-13) | 4.9 | 7.8 | 500.0 | 6.4 | 100.3 | (0.14, 0.14) |
| Ex.(14) | Com.(1-14) | 4.9 | 7.8 | 500.0 | 6.4 | 106.9 | (0.15, 0.13) |
| Ex.(15) | Com.(1-15) | 4.9 | 7.8 | 500.0 | 6.4 | 110.0 | (0.15, 0.14) |
| Ex.(16) | Com.(2-1) | 4.7 | 8.1 | 500.0 | 6.2 | 101.0 | (0.15, 0.14) |
| Ex.(17) | Com.(2-2) | 4.5 | 8.3 | 500.0 | 6.0 | 106.0 | (0.15, 0.13) |
| Ex.(18) | Com.(2-3) | 4.6 | 8.3 | 500.0 | 6.0 | 106.8 | (0.15, 0.13) |
| Ex.(19) | Com.(2-4) | 4.5 | 8.3 | 500.0 | 6.0 | 106.0 | (0.14, 0.14) |
| Ex.(20) | Com.(2-5) | 4.5 | 8.2 | 500.0 | 6.1 | 104.2 | (0.15, 0.14) |
| Ex.(21) | Com.(2-6) | 4.5 | 8.3 | 500.0 | 6.0 | 106.2 | (0.15, 0.14) |
| Ex.(22) | Com.(2-7) | 4.7 | 8.1 | 500.0 | 6.2 | 109.8 | (0.14, 0.14) |
| Ex.(23) | Com.(2-8) | 4.7 | 8.3 | 500.0 | 6.1 | 103.5 | (0.15, 0.13) |
| Ex.(24) | Com.(2-9) | 4.6 | 8.2 | 500.0 | 6.1 | 106.8 | (0.15, 0.16) |
| Ex.(25) | Com.(2-10) | 4.5 | 8.1 | 500.0 | 6.2 | 104.5 | (0.15, 0.14) |
| Ex.(26) | Com.(2-11) | 4.6 | 8.3 | 500.0 | 6.0 | 104.2 | (0.15, 0.13) |
| Ex.(27) | Com.(2-12) | 4.5 | 8.1 | 500.0 | 6.2 | 109.8 | (0.14, 0.14) |
| Ex.(28) | Com.(2-13) | 4.6 | 8.3 | 500.0 | 6.1 | 107.1 | (0.15, 0.13) |
| Ex.(29) | Com.(2-14) | 4.6 | 8.2 | 500.0 | 6.1 | 105.7 | (0.14, 0.14) |
| Ex.(30) | Com.(2-15) | 4.5 | 8.3 | 500.0 | 6.1 | 101.7 | (0.14, 0.14) |
| Ex.(31) | Com.(2-16) | 4.5 | 8.2 | 500.0 | 6.1 | 100.9 | (0.14, 0.14) | from the results of Comparative Examples 2 and 3 or Comparative Example 5 and Examples 1 to 31. As the phenyl group is further substituted in the ortho-position of biphenyl, the conjugation length and coupling angle become smaller, and thus T1 value and bandgap are increased, and the HOMO value becomes deeper. As a result, the ability to block electrons transferred from the light emitting layer is improved, and the exciton is more easily generated in the light emitting layer, and thus the charge balance in the light emitting layer is improved.

Second, it is thanks to a feature of quinazoline substituent. This can be seen from the results of Comparative Examples 2 and 5 or Comparative Examples 3 and 4 and Examples 1 to 31. Comparing the results of Comparative Examples 2 and 5, the results of Comparative Example 5 in which quinazoline was substituted were more superior to those of Comparative Example 2 in which all aryl groups were substituted. Further, comparing the results of Comparative Example 3 and 4, and Examples 1 to 31, the results of Comparative Example 4 in which the heterocyclic group such as dibenzothiophen was substituted were slightly improved compared with Comparative Example 3 in which the general aryl group was substituted. Also, the results of Examples 1 to 31 in which quinazoline was substituted were most excellent.

This is because the compound of the present invention has appropriate HOMO and LUMO energy compared with the comparative compound, and thus charge balance is achieved, and light emission occurs inside the light emitting layer not at the interface of the hole transport layer, as a result, the driving voltage is lowered and efficiency and lifetime are maximized.

In conclusion, it can be confirmed that the compound of the present invention in which terphenyl and quinazoline substituted at ortho and para positions are substituted at the same time, shows superior performance to the conventional analogous compounds.

As described above, it can be confirmed that the properties of the compound vary depending on the type and position of the substituent even in the case of the similar compound, and this serves as a major factor in improving the device performance, as a result, different results are obtained.

[Example 32] Red OLED (Phosphorescent Host)

ITO layer (anode) was formed on a glass substrate, and then 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer. Subsequently, a light emitting layer with a thickness of 30 nm was formed on the hole transport layer by using compound 3-5 of the present invention as a host material and bis-(1-phenylisoquinoline)iridium(III)acetylacetonate (hereinafter, "(piq)$_2$Ir(acac)") as a dopant material in a weight ratio of 95:5.

Next, BAlq was vacuum-deposited with a thickness of 10 nm on the light emitting layer to form a hole blocking layer, and Alq$_3$ was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 33] to [Example 48] Red OLED (Phosphorescent Host)

The OLEDs were fabricated in the same manner as described in Example 32 except that the compounds of the present invention described in Table 5, instead of the compound 3-5 according to Example 32 of the present invention, were used as as a host material of a light emitting layer.

Comparative Example 6

The OLED was fabricated in the same manner as described in Example 32 except that the following Comparative Compound E, instead of the compound 3-5 according to Example 32 of the present invention, was used as as a host material of a light emitting layer.

<Comparative Compound E>

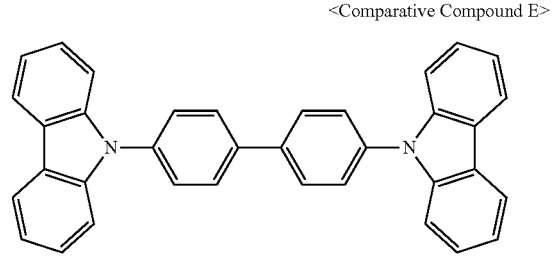 [SMILES: c1ccc2c(c1)c1ccccc1n2-c1ccc(-c2ccc(-n3c4ccccc4c4ccccc43)cc2)cc1]

Electroluminescence (EL) characteristics were measured with a PR-650 (Photoresearch) by applying a forward bias DC voltage to the OLEDs prepared in Examples 32 to 48 of the present invention and Comparative Example 6. And, the T95 life time was measured using a life time measuring apparatus manufactured by Macscience Inc. at reference brightness of 2500 cd/m$^2$. The measurement results are shown in Table 5 below.

TABLE 5

| | Compound A | Compound B | Voltage (V) | Current Density (mA/cm$^2$) | Brightness (cd/m$^2$) | Efficiency (cd/A) | Lifetime T(95) |
|---|---|---|---|---|---|---|---|
| comp. Ex(6) | comp. Com E | — | 6.7 | 34.2 | 2500.0 | 7.3 | 83.4 |
| Ex.(32) | Com. 3-5 | — | 6.1 | 29.1 | 2500.0 | 8.6 | 90.8 |
| Ex.(33) | Com. 1-1 | Com. 3-1 | 5.5 | 18.0 | 2500.0 | 13.9 | 114.4 |
| Ex.(34) | Com. 1-1 | Com. 3-5 | 5.8 | 17.3 | 2500.0 | 14.5 | 114.4 |
| Ex.(35) | Com. 1-1 | Com. 4-4 | 5.7 | 17.5 | 2500.0 | 14.3 | 114.9 |

TABLE 5-continued

|  | Compound A | Compound B | Voltage (V) | Current Density (mA/cm$^2$) | Brightness (cd/m$^2$) | Efficiency (cd/A) | Lifetime T(95) |
|---|---|---|---|---|---|---|---|
| Ex.(36) | Com. 1-1 | Com. 4-14 | 5.7 | 20.5 | 2500.0 | 12.2 | 110.9 |
| Ex.(37) | Com. 1-14 | Com. 3-1 | 5.7 | 18.7 | 2500.0 | 13.4 | 113.1 |
| Ex.(38) | Com. 1-14 | Com. 3-5 | 5.4 | 16.4 | 2500.0 | 15.2 | 110.1 |
| Ex.(39) | Com. 1-14 | Com. 4-4 | 5.7 | 19.0 | 2500.0 | 13.2 | 119.2 |
| Ex.(40) | Com. 1-14 | Com. 4-14 | 5.5 | 19.8 | 2500.0 | 12.6 | 116.2 |
| Ex.(41) | Com. 2-2 | Com. 3-1 | 5.8 | 19.7 | 2500.0 | 12.7 | 115.3 |
| Ex.(42) | Com. 2-2 | Com. 3-5 | 5.7 | 18.6 | 2500.0 | 13.4 | 113.9 |
| Ex.(43) | Com. 2-2 | Com. 4-4 | 5.7 | 20.3 | 2500.0 | 12.3 | 113.7 |
| Ex.(44) | Com. 2-2 | Com. 4-14 | 5.8 | 20.5 | 2500.0 | 12.2 | 113.8 |
| Ex.(45) | Com. 2-4 | Com. 3-1 | 5.7 | 17.2 | 2500.0 | 14.5 | 110.9 |
| Ex.(46) | Com. 2-4 | Com. 3-5 | 5.7 | 20.8 | 2500.0 | 12.0 | 115.1 |
| Ex.(47) | Com. 2-4 | Com. 4-4 | 5.7 | 18.2 | 2500.0 | 13.7 | 119.0 |
| Ex.(48) | Com. 2-4 | Com. 4-14 | 5.7 | 16.8 | 2500.0 | 14.9 | 117.8 |

From the results shown in Table 5 above, it can be seen that OLEDs using a mixture of compounds of the present invention as a host material of a light emitting layer showed a lower driving voltage and remarkably improved luminous efficiency and lifetime than OLED using Comparative Compound E.

That is, it is confirmed that the device results of Example 32 using the compound 3-5 of the present invention alone as a host material were better than those of Comparative Example 6 using the Comparative compound E alone as a host, and Examples 33 to 48 using the mixture of the compounds of the present invention showed remarkably improved lifetime, especially the efficiency, as well as the driving voltage than Example 32.

This is because when the compound of the present invention is used as a host material, physical properties acting as a host material are significantly changed, thereby acting as a main factor for the performance improvement in the device deposition, and thus an improved results are obtained. That is, the device using the compound of the present invention, especially a mixture of the compounds of the present invention showed better results than the device using the Comparative compound E. This indicates that when the mixture of the compounds of the present invention is used as as a host material, the physical properties of the compound and the device result may be significantly different.

Although the exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

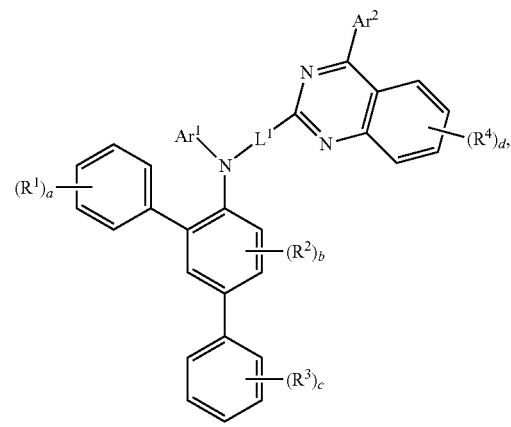

[Formula 1]

wherein
Ar$^1$ and Ar$^2$ are each independently selected from the group consisting of hydrogen, halogen, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group, a C$_6$-C$_{30}$ aryloxy group and -L'-N(R$_a$)(R$_b$), R$^1$ to R$^4$ are each independently selected from the group consisting of hydrogen, deuterium, halogen, S(R$^5$), O(R$^6$), N(R$^7$)(R$^8$), C(R$^9$)(R$^{10}$)(R$^{11}$), a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group, a C$_6$-C$_{30}$ aryloxy group and -L'-N(R$_a$)(R$_b$), neighboring R$^1$ groups, neighboring R$^2$ groups, neighboring R$^3$ groups, or neighboring R$^4$ groups are optionally linked to each other to form a ring, R$^1$ and R$^2$, or R$^2$ and R$^3$ are optionally linked to each other to form a ring, with the proviso that Ar$^1$ and R$^1$, Ar$^1$ and R$^2$, and Are and R$^4$ do not form a ring together, a and c are each an integer of 0 to 5, b is an integer of 0 to 3, d is an integer of 0 to 4, and when each of a, b, c and d is an integer of 2 or more, each of the plurality of $R^1$s to $R^4$s may be the same or different from each other, $L^1$ and L' are each independently selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, $R_a$ and $R_b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, $R^5$ to $R^{11}$ are each independently selected from the group consisting of hydrogen, halogen, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, and a $C_3$-$C_{50}$ alkylacetate group, and the above aryl group, arylene group, flourenyl group, flourenylene group, heterocyclic group, fused ring group, alkyl group, alkenyl group, alkynyl group, alkoxyl group, aryloxyl group, alkylacetate group and a ring formed by linking between neighboring $R^1$ groups, neighboring $R^2$ groups, neighboring $R^3$ groups, neighboring $R^4$ groups, $R^1$ and $R^2$, and $R^2$ and $R^3$ are each optionally further substituted with one or more substituents selected from the group consisting of dueterium, halogen, a silane group, a siloxane group, a boron group, a germanium group, a cyano group, a nitro group, a $C_1$-$C_{20}$alkylthio group, a $C_1$-$C_{20}$ alkoxy group, a $C_1$-$C_{20}$ group, a $C_2$-$C_{20}$ alkenyl group, a $C_2$-$C_{20}$ alkynyl group, a $C_6$-$C_{20}$ aryl group, a $C_6$-$C_{20}$ aryl group substituted with dueterium, a fluorenyl group, a $C_2$-$C_{20}$ hetercyclic group containing at least one heteroatom selected from the group consisting of O, N, S, Si, and P, a $C_3$-$C_{20}$ cycloalkl group, a $C_7$-$C_{20}$ arylalkyl group and a $C_8$-$C_{20}$ arylalkenyl group.

2. The compound of claim 1 represented by one of the following Formulas 2 to 4 and 6:

<Formula 2>

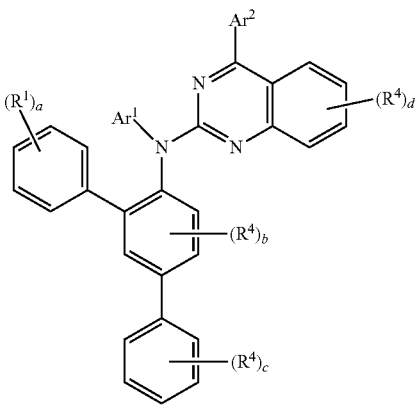

<Formula 3>

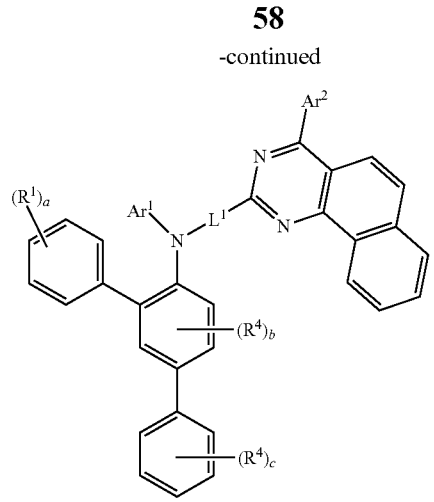

<Formula 4>

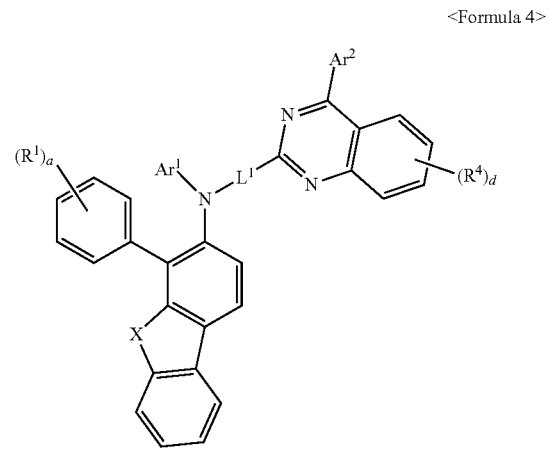

<Formula 6>

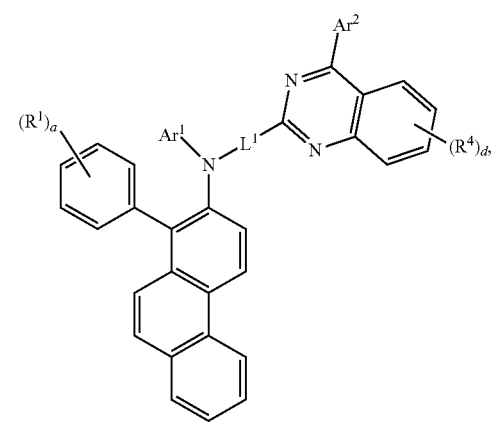

wherein $Ar^1$, $Ar^2$, $L^1$, $R^1$ to $R^4$, a, b, c and d are the same as defined in claim 1, X is O, S, $N(R^{12})$ or $C(R^{13})(R^{14})$, wherein $R^{12}$ to $R^{14}$ are each independently selected from the group consisting of hydrogen, halogen, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{60}$ aryl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, and a $C_3$-$C_{50}$ alkylacetate group, and $R^{13}$ and $R^{14}$ groups are optionally linked to each other to form a ring.
3. The compound of claim 1, wherein Formula 1 is one of the following compounds:
1-1
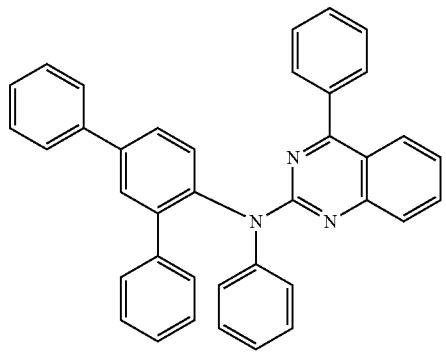
1-2
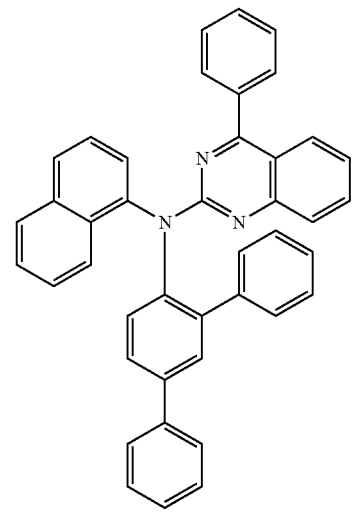
1-3
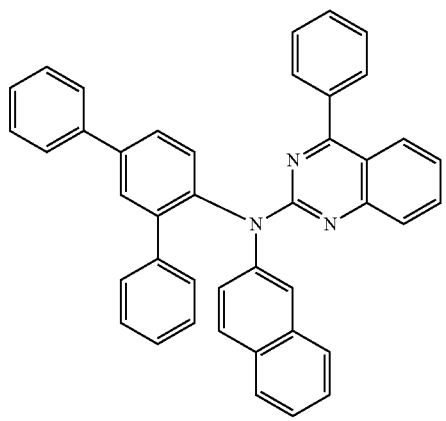
1-4
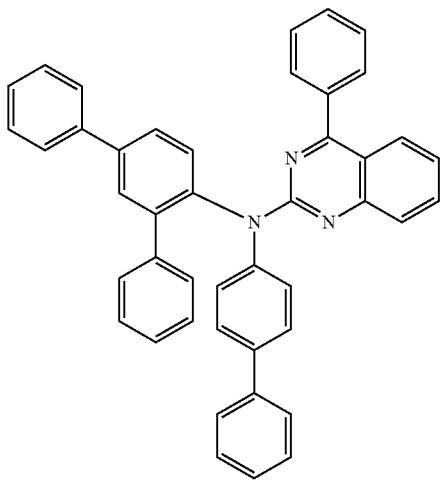
1-5
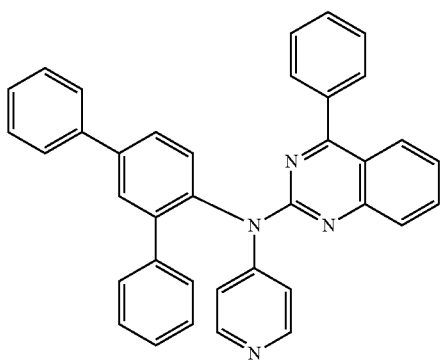
1-6
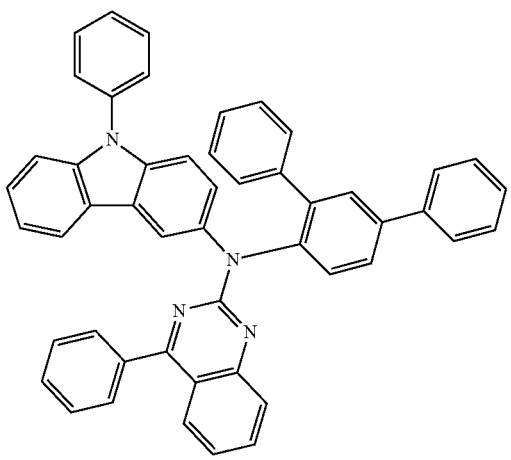

-continued
1-7
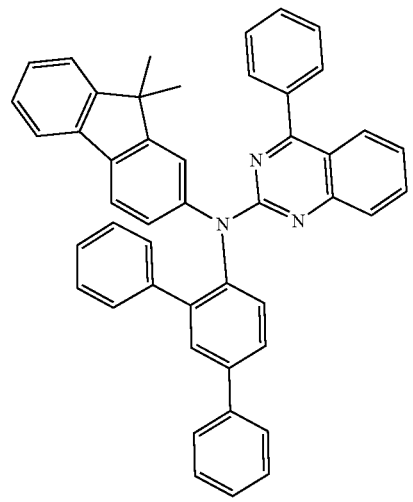
1-8
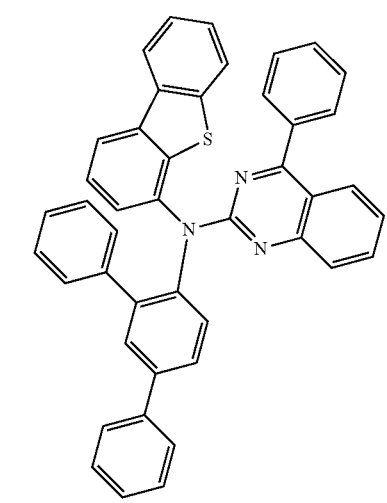
1-9
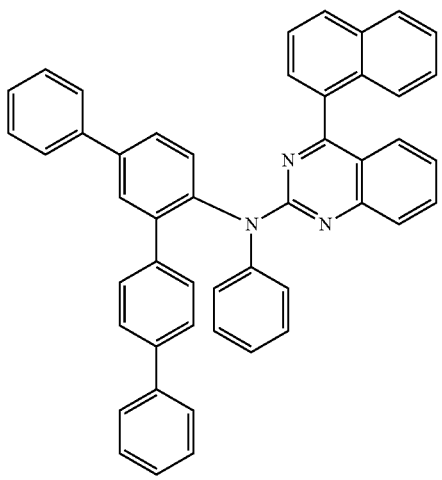
-continued
1-10
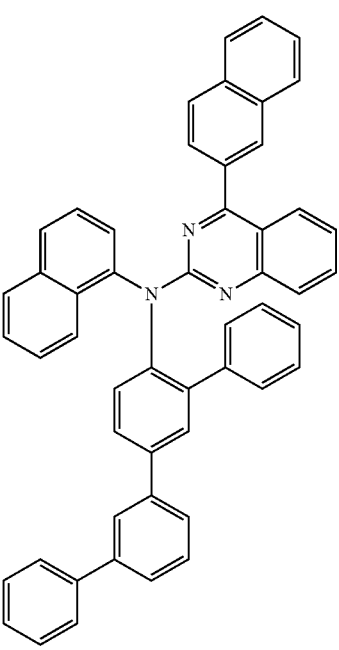
1-11
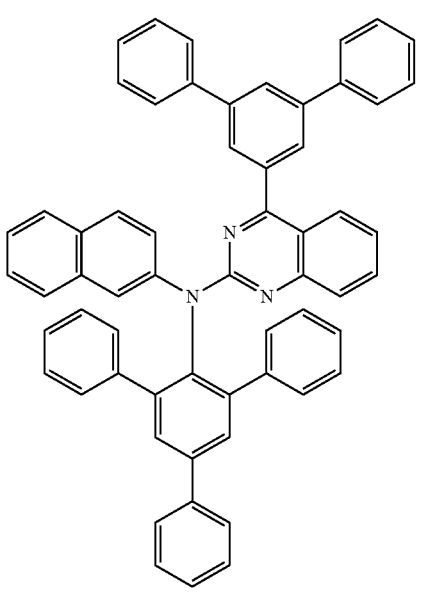
1-12
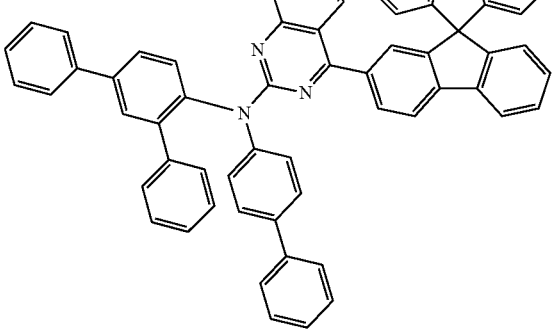

1-13
1-14
1-15
1-16
2-1
2-2

2-3
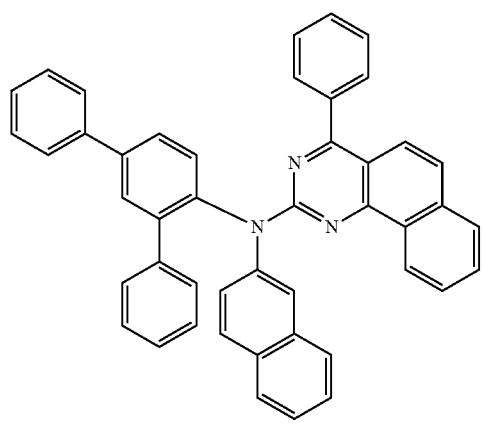
2-4
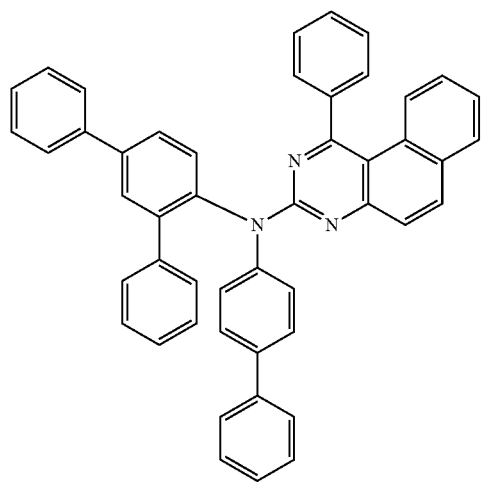
2-5
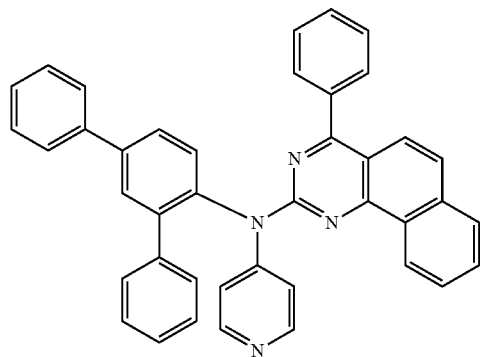
2-6
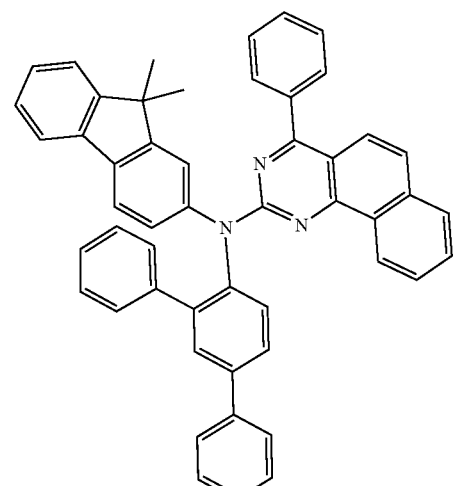
2-7
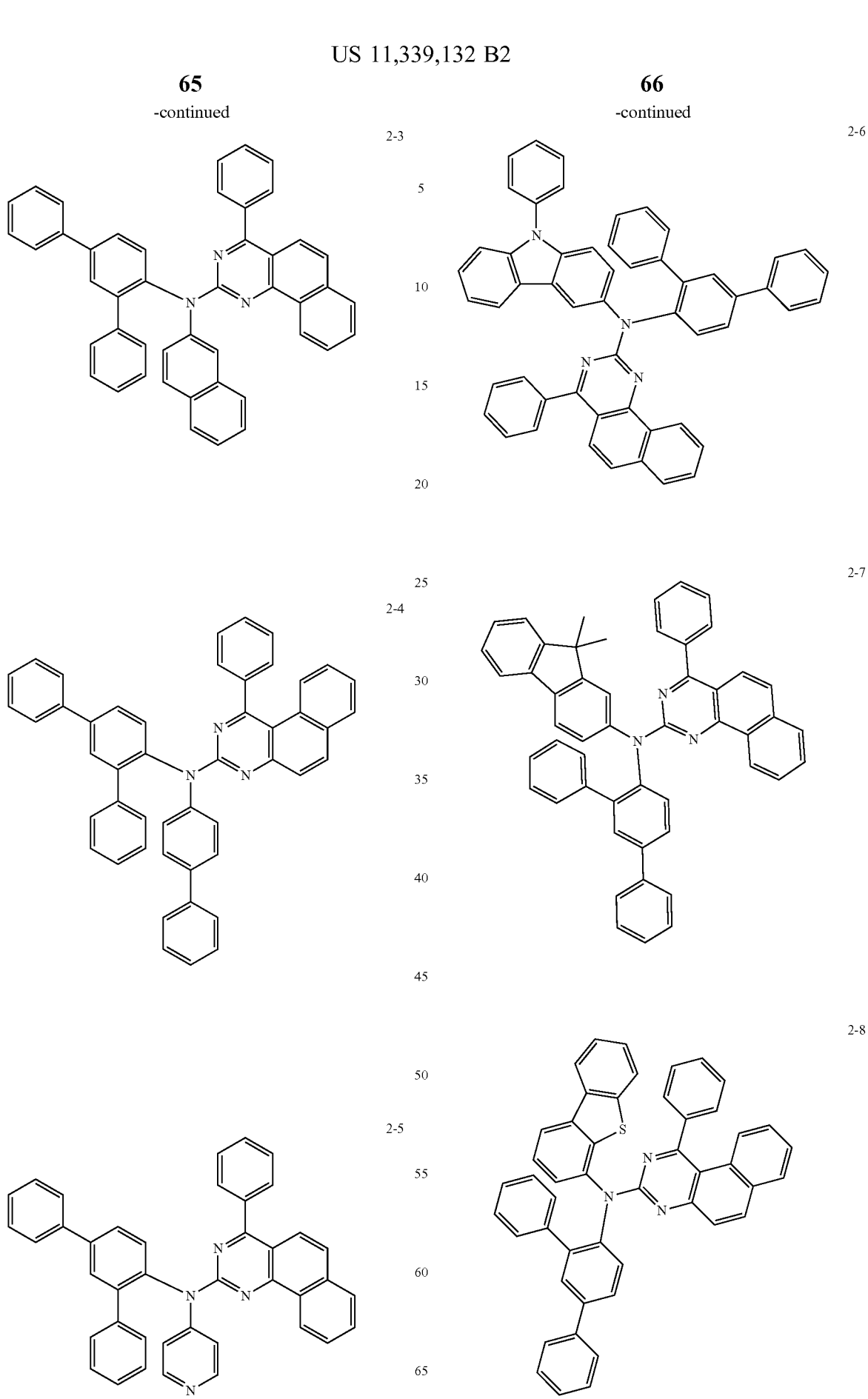
2-8
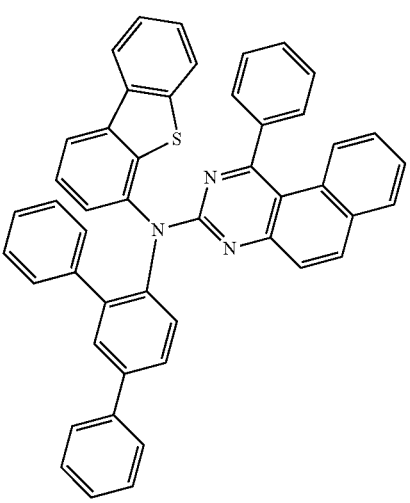

2-9
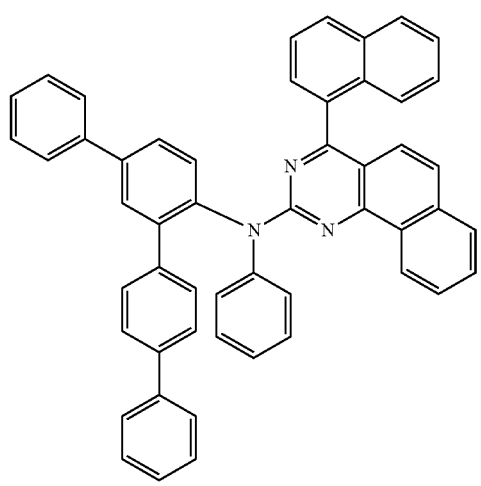
2-11
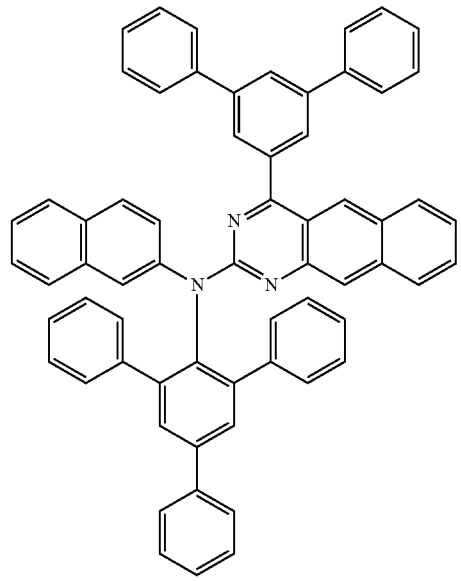
2-10
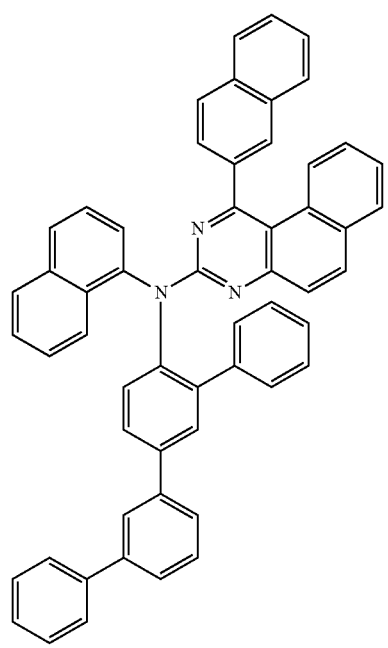
2-12
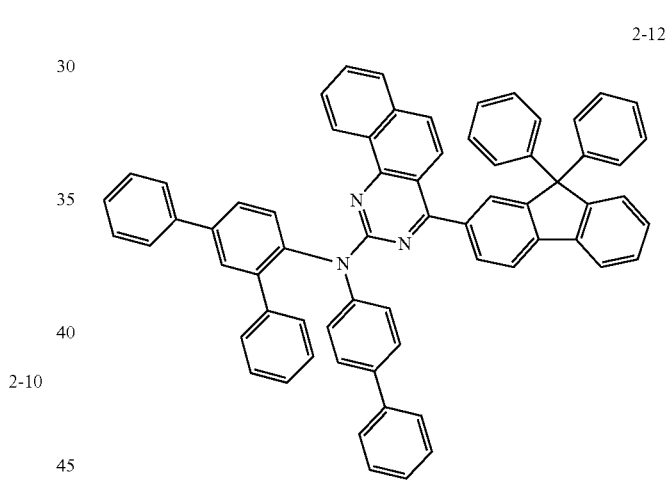
2-13
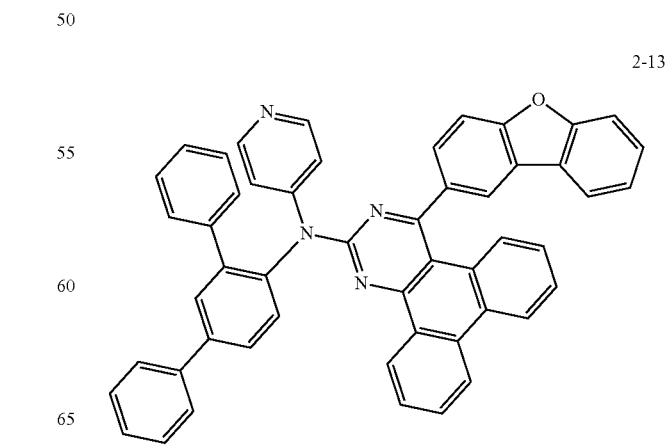

2-14
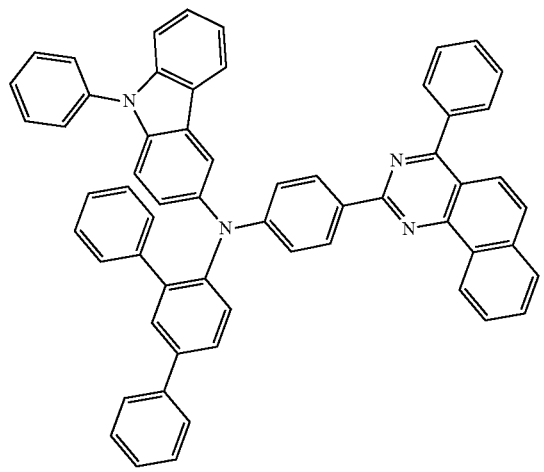
2-15
3-2
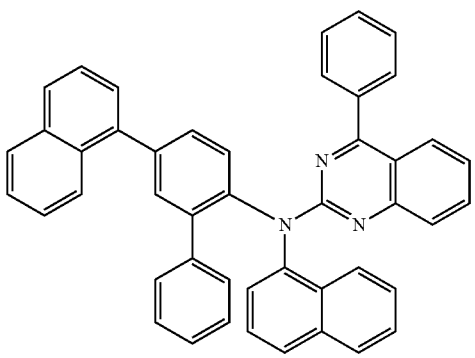
3-3
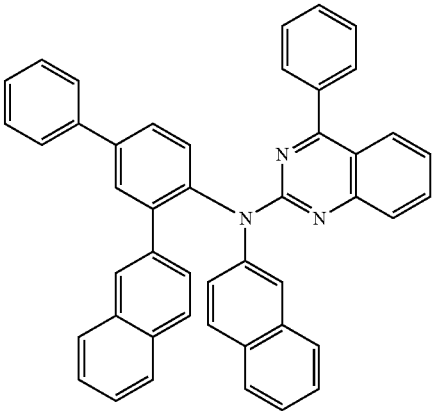
3-5
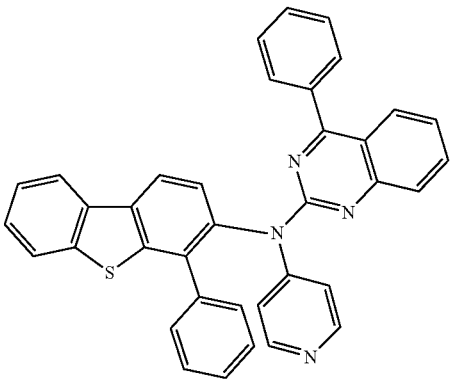
2-16
3-6
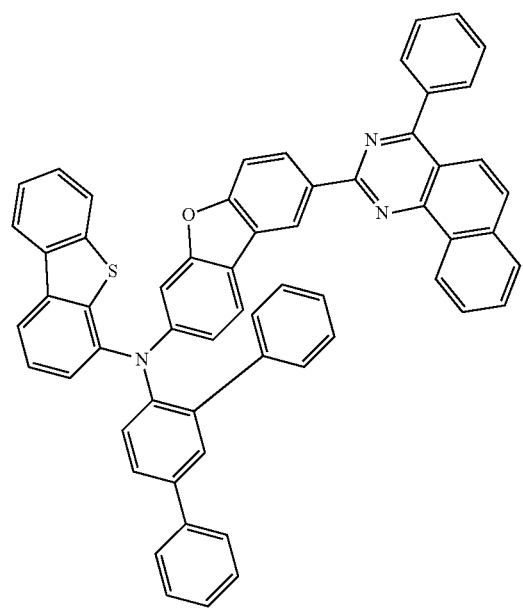
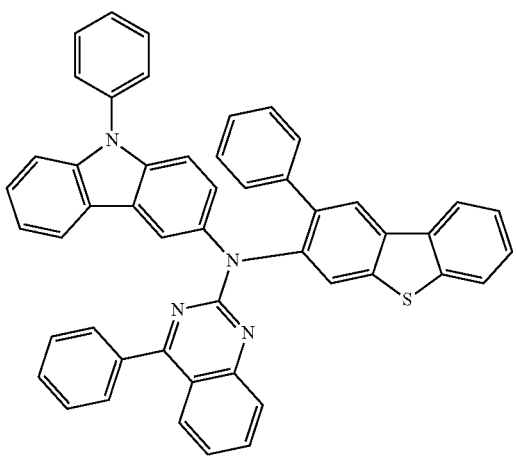

3-7
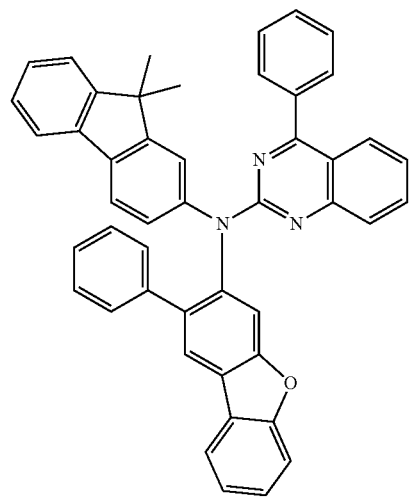
3-8
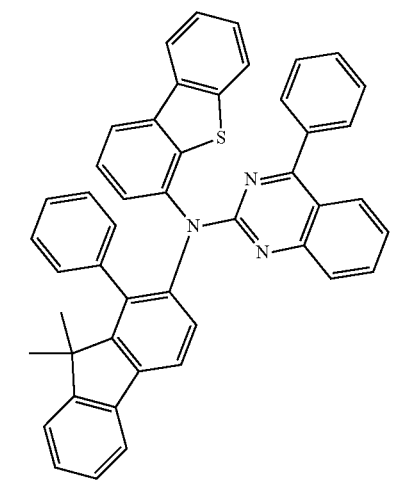
3-10
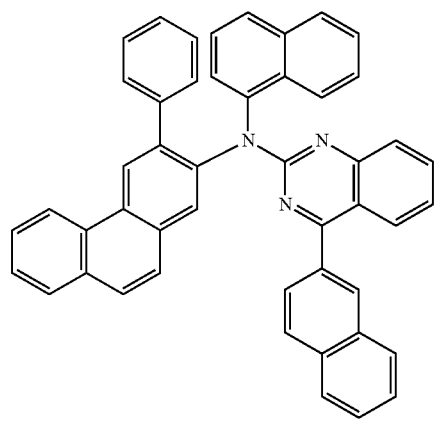
3-11
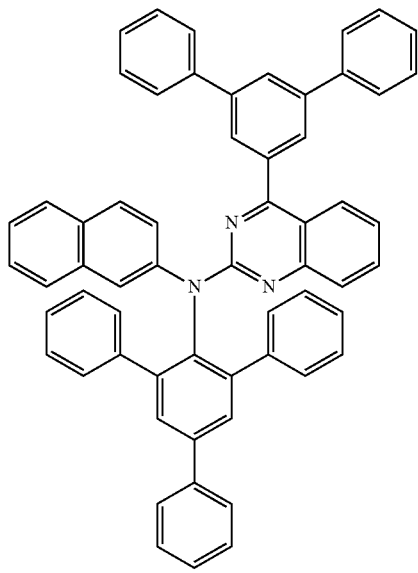
3-12
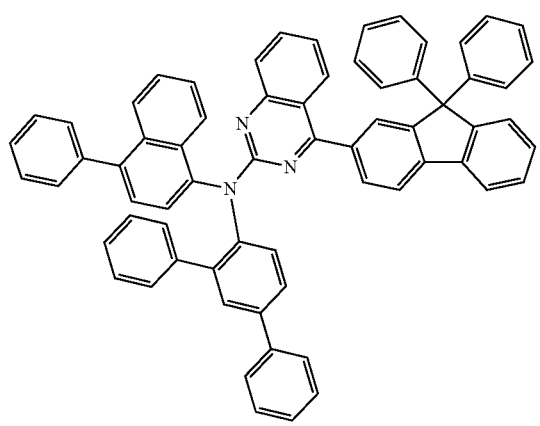
3-14
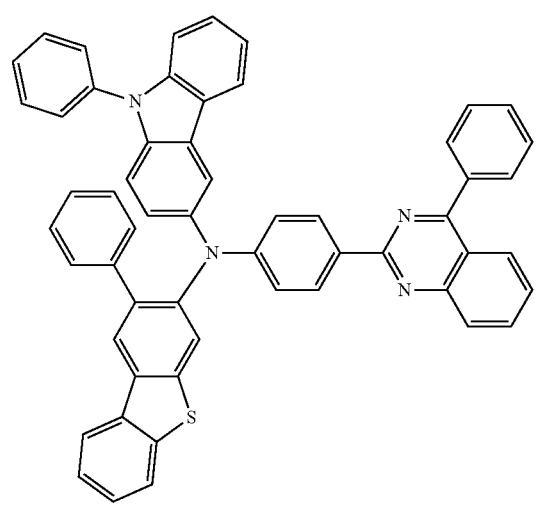

-continued
3-15
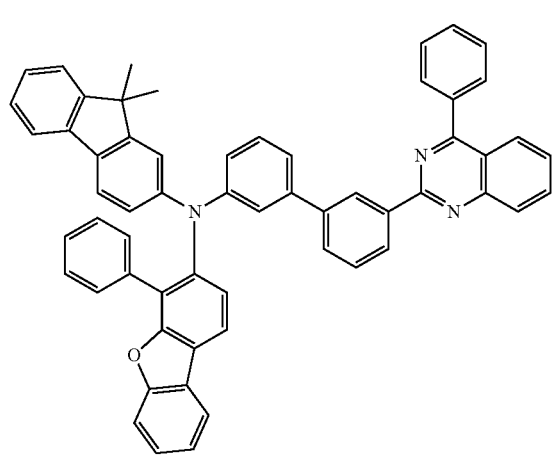
4-3
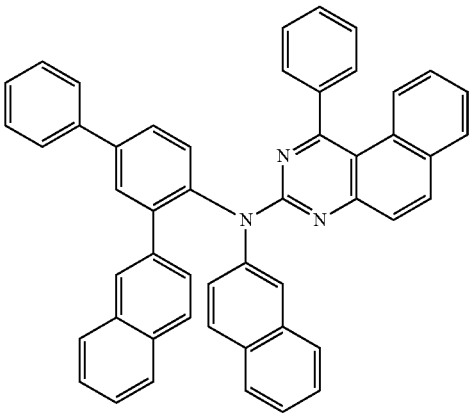
3-16
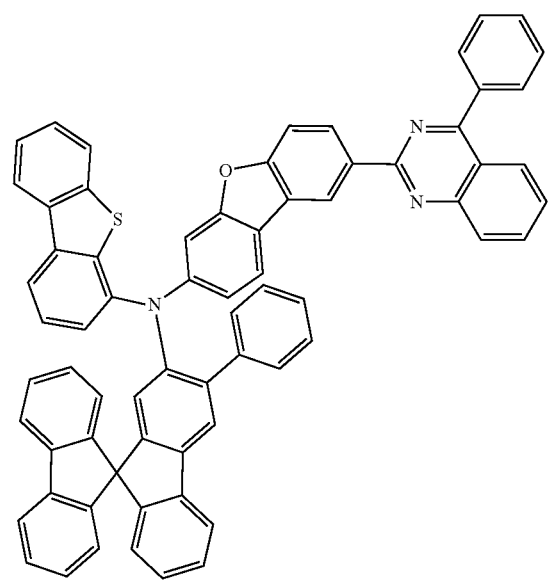
4-5
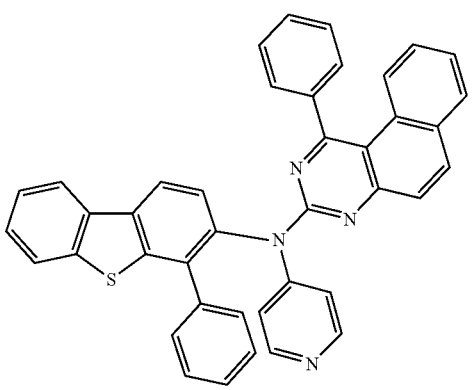
4-2
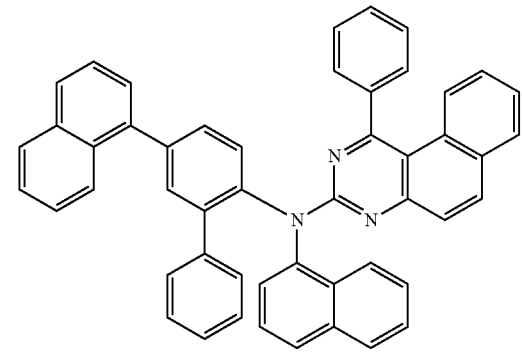
4-6
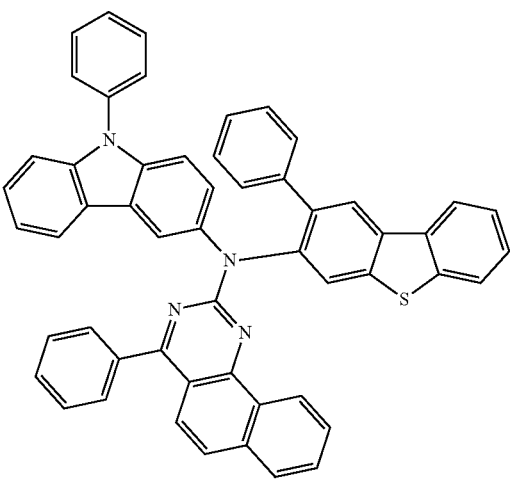

4-7
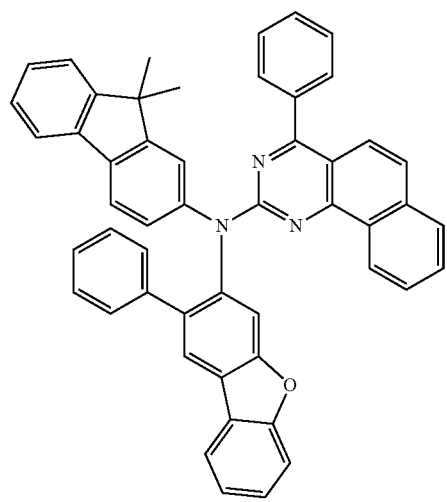
4-8
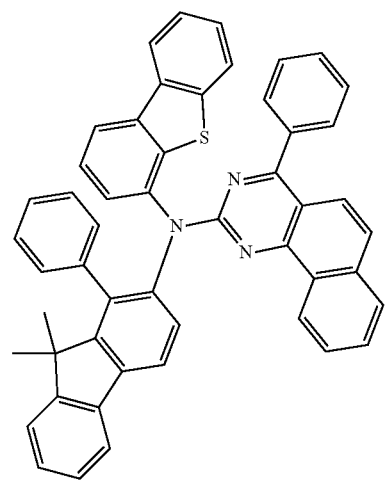
4-10
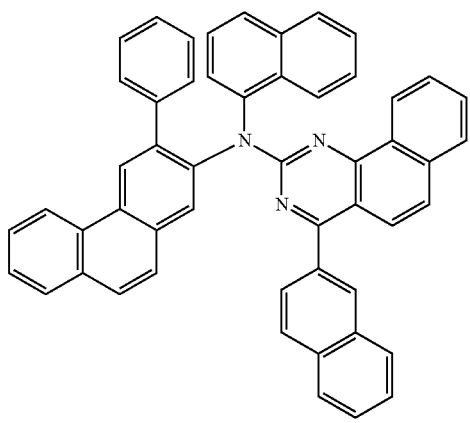
4-11
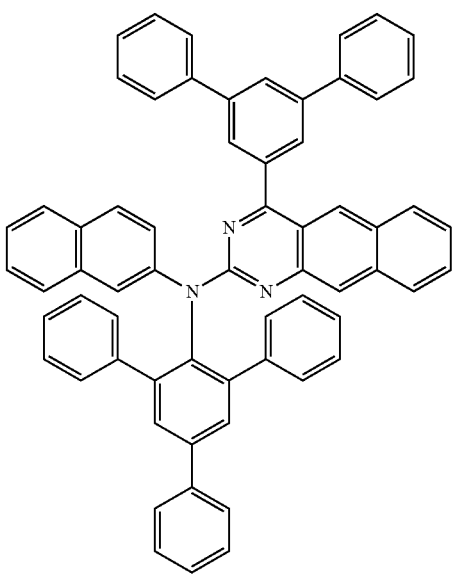
4-12
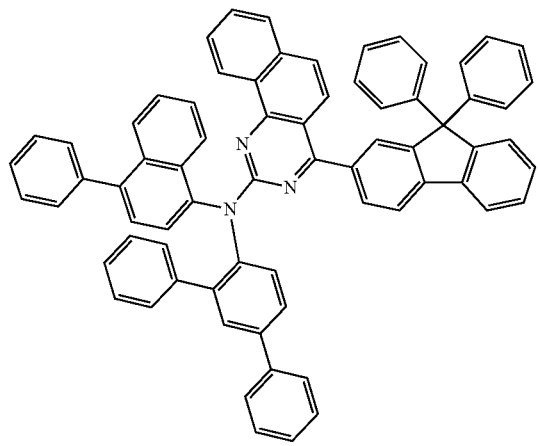
4-14
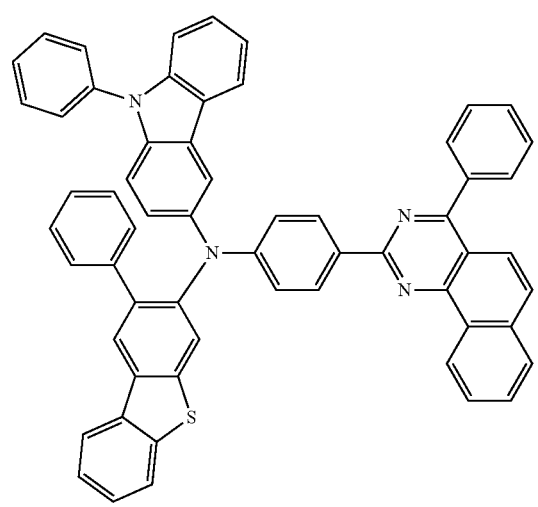

4-15

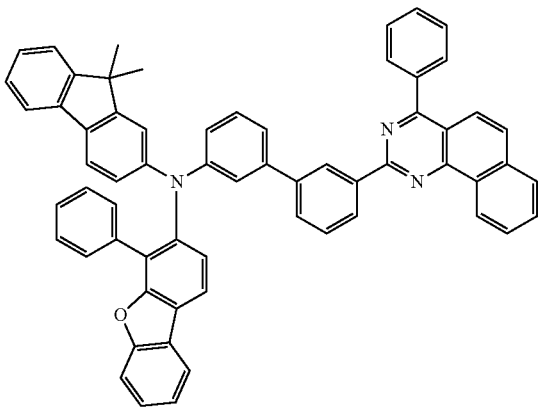

4-16

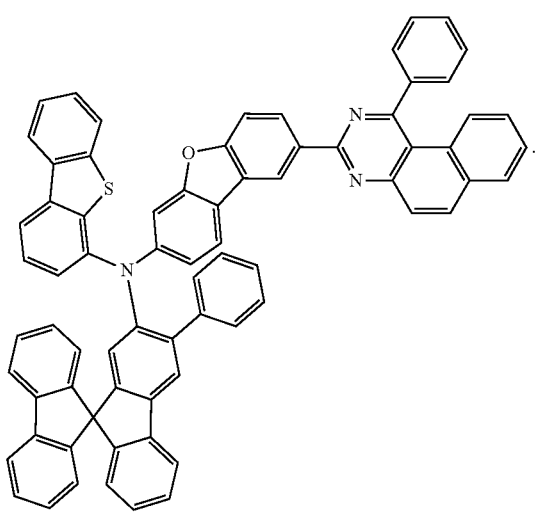

4. An organic electric element comprising a first electrode, a second electrode, and an organic material layer formed between the first electrode and the second electrode, wherein the organic material layer comprises a compound of claim 1.

5. The organic electric element of claim 4, wherein the compound is comprised as a single compound or a mixture of two or more kinds in at least one layer of a hole injection layer, a hole transport layer, an emission-auxiliary layer and a light emitting layer of the organic material layer.

6. The organic electric element of claim 5, wherein the compound is used as phosphorescent host of the light emitting layer.

7. The organic electric element of claim 4 further comprising a layer for improving luminous efficiency formed on at least one side of sides of the first electrode and the second electrode, wherein at least one side is not facing the organic material layer.

8. The organic electric element of claim 4, wherein the organic material layer is formed by any one of the processes of spin coating, nozzle printing, inkjet printing, slot coating, dip coating and roll-to-roll.

9. An electronic device comprising a display device and a control unit for driving the display device, wherein the display device comprises the organic electric element of claim 4.

10. The electronic device of claim 9, wherein the organic electric element is an organic light emitting diode, an organic solar cell, an organic photo conductor, an organic transistor, or an element for monochromatic or white illumination.

* * * * *